US009867801B2

(12) United States Patent
Srinivasan et al.

(10) Patent No.: US 9,867,801 B2
(45) Date of Patent: Jan. 16, 2018

(54) AMORPHOUS SOLID DISPERSION COMPRISING TAXANE, TABLET COMPRISING THE SAME, AND METHOD FOR PREPARING THE SAME

(71) Applicant: HANMI PHARM. CO., LTD., Hwaseong-si, Gyeonggi-do (KR)

(72) Inventors: Shanmugam Srinivasan, Suwon-si (KR); Ho Taek Im, Yongin-si (KR); Young Su Yoon, Seoul (KR); Yong Il Kim, Suwon-si (KR); Jae Hyun Park, Suwon-si (KR); Jong Soo Woo, Suwon-si (KR)

(73) Assignee: HANMI PHARM. CO., LTD., Hwaseong-si, Gyeonggi-do (KR)

( * ) Notice: Subject to any disclaimer, the term of this patent is extended or adjusted under 35 U.S.C. 154(b) by 0 days.

(21) Appl. No.: 15/300,515

(22) PCT Filed: Mar. 20, 2015

(86) PCT No.: PCT/KR2015/002756
§ 371 (c)(1),
(2) Date: Sep. 29, 2016

(87) PCT Pub. No.: WO2015/152544
PCT Pub. Date: Oct. 8, 2015

(65) Prior Publication Data
US 2017/0112799 A1 Apr. 27, 2017

(30) Foreign Application Priority Data

Mar. 31, 2014 (WO) ................ PCT/KR2014/002734

(51) Int. Cl.
| | | |
|---|---|---|
| *A61K 31/337* | (2006.01) | |
| *A61K 9/16* | (2006.01) | |
| *A61K 9/20* | (2006.01) | |
| *A61K 9/10* | (2006.01) | |
| *A61K 9/14* | (2006.01) | |

(52) U.S. Cl.
CPC ............. *A61K 31/337* (2013.01); *A61K 9/10* (2013.01); *A61K 9/146* (2013.01); *A61K 9/1617* (2013.01); *A61K 9/1635* (2013.01); *A61K 9/1694* (2013.01); *A61K 9/2013* (2013.01); *A61K 9/2027* (2013.01); *A61K 9/2054* (2013.01); *A61K 9/2077* (2013.01); *A61K 9/2095* (2013.01)

(58) Field of Classification Search
CPC ...... A61K 31/337; A61K 9/10; A61K 9/1617; A61K 9/1635; A61K 9/1694; A61K 9/2013; A61K 9/2027; A61K 9/2054; A61K 9/2077; A61K 9/2095
USPC ........................................................ 514/341
See application file for complete search history.

(56) References Cited

U.S. PATENT DOCUMENTS

| | | | |
|---|---|---|---|
| 2002/0041896 | A1 | 4/2002 | Straub et al. |
| 2008/0160095 | A1 | 7/2008 | Desai et al. |
| 2009/0054503 | A1 | 2/2009 | Beijnen et al. |

FOREIGN PATENT DOCUMENTS

| | | |
|---|---|---|
| ES | 2 535 401 T3 | 5/2015 |
| WO | 03/043602 A1 | 5/2003 |
| WO | 2007/073389 A1 | 6/2007 |
| WO | 2010/020799 A2 | 2/2010 |
| WO | 2013/040187 A1 | 3/2013 |

OTHER PUBLICATIONS

Kawakami et al., "Microemulsion formulation for enhanced absorption of poorly soluble drugs: I. Prescription design", Journal of Controlled Release, vol. 81, pp. 65-74, (2002).
Kang et al., "Polymeric Delivery Systems for Poorly Soluble Drugs", Encyclopedia of Pharmaceutical Technology, vol. 5, pp. 2913-2924, Informa Healthcare USA, 2007.
Heng et al., "Chapter 14—Rapid Release Granulation", Handbook of Pharmaceutical Granulation Technology, 2nd edition, pp. 407-429, Taylor & Francis Group LLC, 2005.
Handbook of Pharmaceutical Excipients (6th edition, 917 pages, edited by Rowe, Sheskey, and Quinn, published by Pharmaceutical Press and the American Pharmacists Association, 2009).
Correa, "Pautas para el Examen de Patentes Farmaceuticas. Una Perspectivca desde la Salud Pública", 66 pages, 2008.

*Primary Examiner* — Kristin Vajda
(74) *Attorney, Agent, or Firm* — Vorys, Sater, Seymour and Pease LLP; Mih Suhn Koh

(57) ABSTRACT

Provided is an amorphous solid dispersion including a taxane or a pharmaceutically acceptable salt thereof, a pharmaceutically acceptable polymer, and a pharmaceutically acceptable surfactant, which has enhanced solubility. Also provided is a method for preparing the solid dispersion. The present subject matter also provides a tablet having good solubility, bioavailability and stability, which comprises the amorphous solid dispersion, an intragranular excipient, and an extragranular excipient.

33 Claims, 9 Drawing Sheets

AMORPHOUS SOLID DISPERSION COMPRISING TAXANE, TABLET COMPRISING THE SAME, AND METHOD FOR PREPARING THE SAME

FIELD OF THE INVENTION

The present invention relates to an amorphous solid dispersion comprising a taxane or a pharmaceutically acceptable salt thereof, polyvinylpyrrolidone, polysorbate, and sodium lauryl sulfate; a tablet comprising the same; and the methods for preparing the solid dispersion and the tablet.

BACKGROUND OF THE INVENTION

Taxanes are diterpenes produced by the plants of the genus *Taxus*, and are widely used as chemotherapy agents. Examples of taxanes include paclitaxel (Taxol®), docetaxel (Taxotere® or Docecad), cabazitaxel, larotaxel, ortataxel, tesetaxel and the like.

Among them, paclitaxel is one of the most effective antineoplastic agents that has been widely prescribed to treat a wide variety of tumors, including ovarian carcinoma, breast cancer, head and neck cancers, non-small lung cancer, prostatic cancer, and advanced forms of Kaposi's sarcoma. One of the major limitations associated with this potent drug is its low aqueous solubility due to its extremely hydrophobic nature.

The water solubility of paclitaxel is ~10 μg/mL and the lack of functional groups in its chemical structure precluded any possible salt formation to improve its solubility. Therefore, various approaches to solubilize paclitaxel have been carried out for more than a decade and the most successful one is Taxol® (Bristol-Myers Squibb), the commercially available formulation for intravenous administration, which is 6 mg/mL of paclitaxel in a 50:50% v/v mixture of Cremophor EL® and dehydrated ethanol.

However, the clinical application of Taxol® encountered many problems, including serious or even fatal hypersensitivity episodes due to histamine induction by Cremophor EL® and possible precipitation after dilution and leaching of the diethylhexyl phthalate (DEHP) from polyvinylchloride (PVC) infusion sets, necessitating the use of plasticizer-free containers or bags and causing inconvenience to medical staff and pain to patients. Besides, to alleviate the severe side-effects of Taxol® formulation, patients are often required to receive premedication and/or prolonged infusion regimen (up to 24 hours) leading to either inconvenient long infusion time for patients or increased hospitalization cost of the patients for the entire 6 to 24-hour infusion duration. Moreover, such measures normally would not completely eliminate the side effects.

Accordingly, many formulation approaches such as to reduce the infusion time, to increase the stability of formulation, to prepare non-toxic formulations without cremophor or reduced cremophor amount, etc. have been made and disclosed in U.S. Pat. No. 6,569,459 (Method of administration of paclitaxel-plasma protein formulation), U.S. Pat. No. 5,681,846 (Extended stability formulations for paclitaxel), U.S. Pat. No. 6,919,370 (Pharmaceutical formulations comprising paclitaxel, derivatives, and pharmaceutically acceptable salts thereof), U.S. Pat. No. 6,107,333 (Parenteral paclitaxel in a stable non-toxic formulation), etc.

However, in general, an oral formulation is preferred because of the several advantages over other methods of administration, especially intravenous administration. In addition to the flexibility of treatment, oral formulations are inexpensive, convenient and have higher rate of compliance.

Accordingly, there exists a clear need for oral compositions of a taxane including paclitaxel that are easy to prepare and have enhanced solubility and bioavailability.

SUMMARY OF THE INVENTION

The present invention relates to an amorphous solid dispersion comprising a taxane (e.g., paclitaxel or docetaxel) with enhanced solubility, stability, and/or bioavailability.

The present invention also relates to an oral formulation (e.g., a tablet) comprising a taxane with desirable solubility, bioavailability and/or stability, wherein the taxane is in an amorphous solid dispersion.

The present invention also relates to a method for preparing the amorphous solid dispersion.

The present invention also relates to a method for preparing the oral formulation (e.g., a tablet).

The present invention also relates to a method for treating a cell proliferative disease (e.g., a cancer), comprising administering a therapeutically effective amount of the solid dispersion or the oral formulation of the present invention to a subject in need thereof.

The present invention also relates to use of the solid dispersion or the oral formulation of the present invention for treating a cell proliferative disease (e.g., a cancer).

The present invention also relates to use of the solid dispersion or the oral formulation of the present invention in the manufacture of a medicament for treating a cell proliferative disease (e.g., a cancer).

In accordance with one aspect of the present invention, the amorphous solid dispersion comprises a taxane or a pharmaceutically acceptable salt thereof, a pharmaceutically acceptable polymer, and a pharmaceutically acceptable surfactant.

In accordance with another aspect of the present invention, the oral formulation (e.g., a tablet) comprises the amorphous solid dispersion, an intragranular excipient, and an extragranular excipient.

In accordance with another aspect of the present invention, the method for preparing the amorphous solid dispersion comprises the steps:

(a) dissolving a taxane or a pharmaceutically acceptable salt thereof, a pharmaceutically acceptable polymer, and a pharmaceutically acceptable surfactant in a solvent to produce a solution; and (b) drying the solution obtained in step (a).

In some embodiment, the drying in step (b) is carried out by spray drying. In further embodiments, the spray drying is conducted in a fluid bed. In further embodiments, the fluid bed comprises an intragranular excipient.

In accordance with still another aspect of the present invention, the method for preparing the oral formulation (e.g., a tablet), comprises the steps:

(a) dissolving a taxane or a pharmaceutically acceptable salt thereof, a pharmaceutically acceptable polymer, and a pharmaceutically acceptable surfactant in a solvent to produce a solution;

(b) drying the solution obtained in step (a) to produce a solid dispersion;

(c) mixing together the solid dispersion in step (b) with an extragranular excipient; and (d) compressing the mixture in step (c).

In some embodiment, the drying in step (b) is carried out by spray drying. In further embodiments, the spray drying is conducted in a fluid bed. In further embodiments, the fluid bed comprises an intragranular excipient.

Other features and embodiments of the present invention will be apparent from the following description and the appended claims.

DETAILED DESCRIPTION OF THE INVENTION

Figure 1:
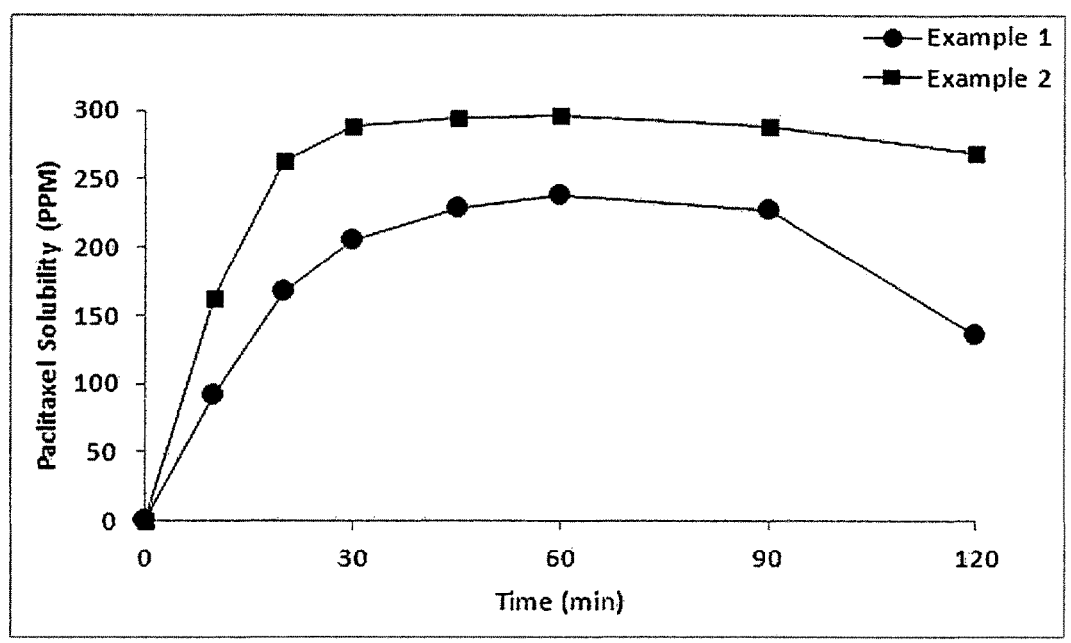
FIG. 1 is a graph showing the solubilities of the solid dispersions of Examples 1 and 2.

The present invention provides an amorphous solid dispersion comprising a taxane or a pharmaceutically acceptable salt thereof, a pharmaceutically acceptable polymer, and a pharmaceutically acceptable surfactant, and a method for preparing the amorphous solid dispersion. Also, the present invention provides an oral formulation comprising the amorphous solid dispersion, an intragranular excipient, and an extragranular excipient, and a method for preparing the oral formulation. The amorphous solid dispersion, the tablet comprising the same, and the methods for preparing the solid dispersion and the oral formulation are described in more detail below.

1. Solid Dispersion According to the Present Invention

Provided in the present invention is a solid dispersion used for delivering a taxane in vivo. In one embodiment, the solid dispersion comprises a taxane or a pharmaceutically acceptable salt thereof, a pharmaceutically acceptable polymer, and a pharmaceutically acceptable surfactant.

(1) Taxane or a Pharmaceutically Acceptable Salt Thereof

A taxane employable in the solid dispersion of the present invention includes, but is not limited to, paclitaxel (Taxol), docetaxel (Taxotere), cabazitaxel, larotaxel, ortataxel, tesetaxel, and a combination thereof. In some embodiments, a taxane is paclitaxel or docetaxel. In further embodiments, the taxane is paclitaxel.

The pharmaceutically acceptable salts of a taxane suitable for use in the solid dispersion of the present invention are conventional non-toxic salts and can include a salt with a base or an acid addition, such as a salt with an inorganic base, for example, an alkali metal salt (e.g., lithium salt, sodium salt, potassium salt, etc.), an alkaline earth metal salt (e.g., calcium salt, magnesium salt, etc.), an ammonium salt; a salt with an organic base, for example, an organic amine salt (e.g., triethylamine salt, pyridine salt, picoline salt, ethanolamine salt, triethanolamine salt, dicyclohexylamine salt, N,N'-dibenzylethylene diamine salt, etc.); an inorganic acid addition salt (e.g., hydrochloride, hydrobromide, sulfate, phosphate, etc.); an organic carboxylic or sulfonic acid addition salt (e.g., formate, acetate, trifluoroacetate, maleate, tartrate, methanesulfonate, benzenesulfonate, p-toluenesulfonate, etc.); a salt with a basic or acidic amino acid (e.g., arginine, aspartic acid, glutamic acid, etc.); and the like.

In some embodiments, the solid dispersion comprises a taxane (e.g., paclitaxel or docetaxel) in the amount of 25-35 mg, 28-32 mg, or 29-31 mg. In further embodiments, the solid dispersion comprises about 30 mg (e.g., 29.5-30.5 mg) taxane.

(2) Pharmaceutically Acceptable Polymer

A pharmaceutically acceptable polymer employable as an additive in the solid dispersion may be a hydrophilic carrier polymer, which includes, but is not limited to, cellulose based polymers (e.g., hydroxypropylmethyl cellulose (HPMC, hypromellose), ethyl cellulose, hydroxyethyl cellulose, hydroxyethylmethyl cellulose, hydroxypropyl cellulose, hypromellose phthalate, cellulose acetate, cellulose acetate phthalate, methylcellulose, ethylcellulose, cellulose, carboxymethylcellulose, microcrystalline cellulose, silicified microcrystalline cellulose, etc.), starch based polymers (e.g., hydroxypropyl starch, starches (including starches from any source, such as corn, potato, rice, wheat, which can be fully pregelatinized and partially gelatinized)), polyethylene glycol, polyacrylic acid, polyacrylamide, polyethylene oxide, polyvinylpyrrolidone, polyvinylalcohol, polyglycolized glycerides, polymethacrylates, hydrocolloids (e.g., carrageenan, chitosan, alginic acid, hyaluronic acid, pectinic acid, etc.).

In some embodiments, polyvinylpyrrolidone may be employed as a representative pharmaceutically acceptable polymer in the solid dispersion of the present invention. The polyvinylpyrrolidone may be a water-soluble polyvinylpyrrolidone having an average molecular weight of 2,000 or more, preferably 20,000 or more. Examples of the polyvinylpyrrolidone used in the present invention include Kollidon 12 PF (BASF, M.W. 2,000~3,000), PVP K-15 (Ashland, M.W. 6,000~15,000), Kollidon 25 (M.W. 28,000~34,000), Kollidon 25 (M.W. 44,000~54,000), PVP K-30 (M.W. 40,000~80,000), PVP K-60 (M.W. 240,000~450,000), Kollidon 90F (M.W. 1,000,000~1,500,000), PVP K-90 (M.W. 900,000~1,500,000), PVP K-120 (M.W. 2,000,000~3,000,000) and the like. In some embodiments, the polyvinylpyrrolidone is Kollidon 25, Kollidon 25 or polyvinylpyrrolidone K-30 (PVP K-30), in particular PVP K-30 which can be obtained commercially.

The weight ratio of the pharmaceutically acceptable polymer (e.g., polyvinylpyrrolidone) and the taxane (e.g., paclitaxel) may be in the range of 2:1 to 9:1, 2:1 to 5:1, 2:1 to 4:1, 2.5:1 to 3.5:1, 2.6:1 to 3.4:1, 2.7:1 to 3.3:1, 2.8:1 to 3.2:1, or 2.9:1 to 3.1:1. In further embodiments, the weight ratio is 2.8:1 to 3.2:1 or 2.9:1 to 3.1:1. In further embodiments, the weight ratio is about 3:1.

The pharmaceutically acceptable polymer (e.g., polyvinylpyrrolidone) may be used in an amount of 10% to 80% by weight based on the total amount of the solid dispersion. In further embodiments, the polyvinylpyrrolidone is employed in an amount of 40% to 60% by weight based on the total amount of the solid dispersion. In further embodiments, the polyvinylpyrrolidone is employed in an amount of about 50% (e.g., 45% to 55%) by weight based on the total amount of the solid dispersion.

In some embodiments, the solid dispersion comprises a pharmaceutically acceptable polymer (e.g., polyvinylpyrrolidone) in the amount of 60-180 mg, 70-150 mg, 80-120 mg, or 85-100 mg. In further embodiments, the solid dispersion comprises about 90 mg (e.g., 85-95 mg) pharmaceutically acceptable polymer.

(3) Pharmaceutically Acceptable Surfactant

A pharmaceutically acceptable surfactant employable as an additive in the solid dispersion includes, but is not limited to, polysorbate (e.g., polysorbate 20, polysorbate 40, polysorbate 80, polysorbate 85, polysorbate 60, etc.), polyoxyl 20 stearate, polyoxyl 35 castor oil, poloxamer, polyoxyethylene sorbitan monoisostearate, polyethylene glycol 40 sorbitan diisostearate, polyoxyl 40 hydrogenated castor oil, poloxamer 331, polyoxyethylene fatty acid esters, polyoxyl 40 castor oil, poloxamer 188, polyoxyethylene polyoxypropylene 1800, oleic acid, sodium desoxycholate, sodium lauryl sulfate, sorbitan monolaurate, sorbitan monooleate, sorbitan monopalmitate, sorbitan trioleate, N-carbamoyl methoxypolyethylene glycol 2000-1,2-distearol, myristic acid, steareth, stearic acid, polyoxyl 40 stearate, polyoxyl 60 stearate, sucrose stearate, tocopherol, polyoxyl castor oil, triglyceride synthetic, trimyristin, tristearin, magnesium stearate, lecithin, lauryl sulfate, vitamin E, egg yolk phosphatides, docusate sodium, dimyristoyl phosphatidylglycerol, dimyristoyl lecithin, Capryol 90 (propylene glycol monocaprylate), Capryol PGMC (propylene glycol monocaprylate), deoxycholate, cholesterol, Cremophor EL, Propylene glycol alginate, Croval A-10 (PEG 60 almond glycerides), Labrafil 1944 (oleoyl macrogol-6 glycerides), Labrafil 2125 (linoleoyl macrogol-6 glycerides), Labrasol (caprylocaproyl macrogol-8 glycerides), Lauroglycol 90 (propylene glycol monolaurate), Lauroglycol FCC (propylene glycol laurate), calcium stearate, Lecithin Centromix E, Lecithin Centrophase 152, Lecithin Centrol 3F21B, POE 26 glycerin, Olepal isosteariques (PEG-6 isostearate), Plurol diisostearique (polyglycerol-3-diisostearate), Plurol Oleique CC, POE 20 Sorbitan trioleate, Tagat TO (polyoxyethylene glycerol trioleate), or Solutol (Macrogol-15 hydroxystearate), or a mixture thereof.

In some embodiments, the pharmaceutically acceptable surfactant is Labrasol, polysorbate 20, polysorbate 80, PEG-Vitamin E, sodium lauryl sulfate, or cremophor, or a mixture thereof. In further embodiments, the pharmaceutically acceptable surfactant is polysorbate or sodium lauryl sulfate, or a mixture thereof. In further embodiments, the pharmaceutically acceptable surfactant is polysorbate 80 or sodium lauryl sulfate, or a mixture thereof. In further embodiments, the pharmaceutically acceptable surfactant is a mixture of polysorbate, for example polysorbate 80, and sodium lauryl sulfate.

The weight ratio of polysorbate to sodium lauryl sulfate may be in the range of 5:1 to 1:5, 4:1 to 1:4, 3:1 to 1:3, 2.5:1 to 1:2.5, 2:1 to 1:2, 1.8:1 to 1:1.8, 1.5:1 to 1:1.5, 1.2:1 to 1:1.2, or 1.1:1 to 1:1.1. In some embodiments, the weight ratio is 1.5:1 to 1:1.5, 1.2:1 to 1:1.2, or 1.1:1 to 1:1.1. In further embodiments, the weight ratio is 1.1:1 to 1:1.1. In further embodiments, the weight ratio is about 1:1.

The weight ratio of the taxane to the pharmaceutically acceptable surfactant may be in the range of 1:1 to 1:3, 1:1.5 to 1:2.5, 1:1.8 to 1:2.2, or 1:1.9 to 1:2.1. In further embodiments, the weight ratio is 1:1.8 to 1:2.2 or 1:1.9 to 1:2.1. In further embodiments, the weight ratio is about 1:2.

The weight of the pharmaceutically acceptable surfactant (e.g., the combined weight of polysorbate and sodium lauryl sulfate) may be 10% to 50% based on the total amount of the solid dispersion. In some embodiments, the weight of the pharmaceutically acceptable surfactant (e.g., the combined weight of polysorbate and sodium lauryl sulfate) is 20% to 40% based on the total amount of the solid dispersion. In further embodiments, the weight of the pharmaceutically acceptable surfactant (e.g., the combined weight of polysorbate and sodium lauryl sulfate) is 30% to 40% based on the total amount of the solid dispersion. In further embodiments, the weight of the pharmaceutically acceptable surfactant (e.g., the combined weight of polysorbate and sodium lauryl sulfate) is about 33% (e.g., 30% to 36%) based on the total amount of the solid dispersion.

In some embodiments, the weight ratio among the taxane, the polysorbate (e.g., polysorbate 80), and sodium lauryl sulfate is 1:1:1 to 1:1:3, 1:2:1 to 1:2:3, 1:3:1 to 1:3:3, 1:1:1 to 1:3:1, 1:1:2 to 1:3:2, or 1:1:3 to 1:3:3. In further embodiments, the weight ratio is 1:1:1 to 1:1:2, 1:1:1 to 1:1:1.5, 1:1:1 to 1:1:1.2, or 1:1:1 to 1:1:1.1. In other further embodiments, the weight ratio is 1:2:1 to 1:2:2, 1:2:1 to 1:2:1.5, 1:2:1 to 1:2:1.2, or 1:2:1 to 1:2:1.1. In other further embodiments, the weight ratio is 1:3:1 to 1:3:2, 1:3:1 to 1:3:1.5, 1:3:1 to 1:3:1.2, or 1:3:1 to 1:3:1.1. In other further embodiments, the weight ratio is 1:1:1 to 1:2:1, 1:1:1 to 1:1.5:1, 1:1:1 to 1:1.2:1, or 1:1:1 to 1:1.1:1. In other further embodiments, the weight ratio is 1:1:2 to 1:2:2, 1:1:2 to 1:1.5:2, 1:1:2 to 1:1.2:2, or 1:1:2 to 1:1.1:2. In other further embodiments, the weight ratio is 1:1:3 to 1:2:3, 1:1:3 to 1:1.5:3, 1:1:3 to 1:1.2:3, or 1:1:3 to 1:1.1:3. In further embodiments, the weight ratio is about 1:1:1.

In some embodiments, the solid dispersion comprises a pharmaceutically acceptable surfactant in the amount of 30-90 mg, 45-75 mg, 50-70 mg, or 55-65 mg. In further embodiments, the solid dispersion comprises about 60 mg (e.g., 58-62 mg) pharmaceutically acceptable surfactant.

In some embodiments, the solid dispersion comprises a polysorbate (e.g., polysorbate 80) in the amount of 0-60 mg, 15-45 mg, 20-40 mg, or 25-35 mg. In further embodiments, the solid dispersion comprises about 30 mg (e.g., 28-32 mg) polysorbate (e.g., polysorbate 80).

In some embodiments, the solid dispersion comprises sodium lauryl sulfate in the amount of 0-60 mg, 15-45 mg, 20-40 mg, or 25-35 mg. In further embodiments, the solid dispersion comprises about 30 mg (e.g., 28-32 mg) sodium lauryl sulfate.

In some embodiments, the solid dispersion comprises a taxane or a pharmaceutically acceptable salt thereof, a pharmaceutically acceptable polymer, and a pharmaceutically acceptable surfactant, wherein the weight ratio of the pharmaceutically acceptable polymer to the taxane is in the range of 2:1 to 9:1 and the weight ratio of the taxane to the pharmaceutically acceptable surfactant is in the range of 1:1 to 1:3, 1:1.5 to 1:2.5, 1:1.8 to 1:2.2, or 1:1.9 to 1:2.1. In further embodiments, the weight ratio of the pharmaceutically acceptable polymer to the taxane is in the range of 2:1 to 5:1. In further embodiments, the weight ratio of the pharmaceutically acceptable polymer to the taxane is in the range of 2:1 to 4:1. In further embodiments, the weight ratio of the pharmaceutically acceptable polymer to the taxane is in the range of 2.5:1 to 3.5:1. In further embodiments, the weight ratio of the pharmaceutically acceptable polymer to the taxane is in the range of 2.6:1 to 3.4:1. In further embodiments, the weight ratio of the pharmaceutically acceptable polymer to the taxane is in the range of 2.7:1 to 3.3:1. In further embodiments, the weight ratio of the pharmaceutically acceptable polymer to the taxane is in the range of 2.8:1 to 3.2:1. In further embodiments, the weight ratio of the pharmaceutically acceptable polymer to the taxane is in the range of 2.9:1 to 3.1:1. In further embodiments, the weight ratio of the pharmaceutically acceptable polymer to the taxane is about 3:1.

In some embodiments, the solid dispersion comprises a taxane or a pharmaceutically acceptable salt thereof, a pharmaceutically acceptable polymer, and a pharmaceutically acceptable surfactant, wherein the weight ratio of the pharmaceutically acceptable polymer to the taxane is in the range of 2:1 to 9:1, 2:1 to 5:1, 2:1 to 4:1, 2.5:1 to 3.5:1, 2.6:1 to 3.4:1, 2.7:1 to 3.3:1, 2.8:1 to 3.2:1, or 2.9:1 to 3.1:1 and the weight ratio of the taxane to the pharmaceutically acceptable surfactant is in the range of 1:1 to 1:3. In further embodiments, the weight ratio of the taxane to the pharmaceutically acceptable surfactant is 1:1.5 to 1:2.5. In further embodiments, the weight ratio of the taxane to the pharmaceutically acceptable surfactant is 1:1.8 to 1:2.2. In further embodiments, the weight ratio of the taxane to the pharmaceutically acceptable surfactant is 1:1.9 to 1:2.1. In further embodiments, the weight ratio of the taxane to the pharmaceutically acceptable surfactant is about 1:2.

In some embodiments, the solid dispersion comprises a taxane or a pharmaceutically acceptable salt thereof, a pharmaceutically acceptable polymer, and a pharmaceutically acceptable surfactant, wherein the weight ratio of the pharmaceutically acceptable polymer to the taxane is about 3:1 and the weight ratio of the taxane to the pharmaceutically acceptable surfactant is about 1:2.

In some embodiments, the solid dispersion comprises a taxane (e.g., paclitaxel or docetaxel) in the amount of 25-35 mg, a pharmaceutically acceptable polymer (e.g., polyvinylpyrrolidone) in the amount of 60-180 mg, a polysorbate (e.g., polysorbate 80) in the amount of 0-60 mg, and sodium lauryl sulfate in the amount of 0-60 mg. In further embodiments, the solid dispersion comprises a taxane (e.g., paclitaxel or docetaxel) in the amount of 28-32 mg. In further embodiments, the solid dispersion comprises a taxane (e.g., paclitaxel or docetaxel) in the amount of 29-31 mg. In further embodiments, the solid dispersion comprises about 30 mg (e.g., 29.5-30.5 mg) taxane.

In some embodiments, the solid dispersion comprises a taxane (e.g., paclitaxel or docetaxel) in the amount of 25-35 mg, a pharmaceutically acceptable polymer (e.g., polyvinylpyrrolidone) in the amount of 70-150 mg, a polysorbate (e.g., polysorbate 80) in the amount of 0-60 mg, and sodium lauryl sulfate in the amount of 0-60 mg. In further embodiments, the solid dispersion comprises a taxane (e.g., paclitaxel or docetaxel) in the amount of 28-32 mg. In further embodiments, the solid dispersion comprises a taxane (e.g., paclitaxel or docetaxel) in the amount of 29-31 mg. In further embodiments, the solid dispersion comprises about 30 mg (e.g., 29.5-30.5 mg) taxane.

In some embodiments, the solid dispersion comprises a taxane (e.g., paclitaxel or docetaxel) in the amount of 25-35 mg, a pharmaceutically acceptable polymer (e.g., polyvinylpyrrolidone) in the amount of 80-120 mg, a polysorbate (e.g., polysorbate 80) in the amount of 0-60 mg, and sodium lauryl sulfate in the amount of 0-60 mg. In further embodiments, the solid dispersion comprises a taxane (e.g., paclitaxel or docetaxel) in the amount of 28-32 mg. In further embodiments, the solid dispersion comprises a taxane (e.g., paclitaxel or docetaxel) in the amount of 29-31 mg. In further embodiments, the solid dispersion comprises about 30 mg (e.g., 29.5-30.5 mg) taxane.

In some embodiments, the solid dispersion comprises a taxane (e.g., paclitaxel or docetaxel) in the amount of 25-35 mg, a pharmaceutically acceptable polymer (e.g., polyvinylpyrrolidone) in the amount of 85-100 mg, a polysorbate (e.g., polysorbate 80) in the amount of 0-60 mg, and sodium lauryl sulfate in the amount of 0-60 mg. In further embodiments, the solid dispersion comprises a taxane (e.g., paclitaxel or docetaxel) in the amount of 28-32 mg. In further embodiments, the solid dispersion comprises a taxane (e.g., paclitaxel or docetaxel) in the amount of 29-31 mg. In further embodiments, the solid dispersion comprises about 30 mg (e.g., 29.5-30.5 mg) taxane.

In some embodiments, the solid dispersion comprises a taxane (e.g., paclitaxel or docetaxel) in the amount of 25-35 mg, a pharmaceutically acceptable polymer (e.g., polyvinylpyrrolidone) in the amount of about 90 mg (e.g., 85-95 mg), a polysorbate (e.g., polysorbate 80) in the amount of 0-60 mg, and sodium lauryl sulfate in the amount of 0-60 mg. In further embodiments, the solid dispersion comprises a taxane (e.g., paclitaxel or docetaxel) in the amount of 28-32 mg. In further embodiments, the solid dispersion comprises a taxane (e.g., paclitaxel or docetaxel) in the amount of 29-31 mg. In further embodiments, the solid dispersion comprises about 30 mg (e.g., 29.5-30.5 mg) taxane.

In some embodiments, the solid dispersion comprises a taxane (e.g., paclitaxel or docetaxel) in the amount of 25-35 mg, a pharmaceutically acceptable polymer (e.g., polyvinylpyrrolidone) in the amount of 60-180 mg, a polysorbate (e.g., polysorbate 80) in the amount of 15-45 mg, and sodium lauryl sulfate in the amount of 0-60 mg. In further embodiments, the solid dispersion comprises a taxane (e.g., paclitaxel or docetaxel) in the amount of 28-32 mg. In further embodiments, the solid dispersion comprises a taxane (e.g., paclitaxel or docetaxel) in the amount of 29-31 mg. In further embodiments, the solid dispersion comprises about 30 mg (e.g., 29.5-30.5 mg) taxane.

In some embodiments, the solid dispersion comprises a taxane (e.g., paclitaxel or docetaxel) in the amount of 25-35 mg, a pharmaceutically acceptable polymer (e.g., polyvinylpyrrolidone) in the amount of 60-180 mg, a polysorbate (e.g., polysorbate 80) in the amount of 20-40 mg, and sodium lauryl sulfate in the amount of 0-60 mg. In further embodiments, the solid dispersion comprises a taxane (e.g., paclitaxel or docetaxel) in the amount of 28-32 mg. In further embodiments, the solid dispersion comprises a taxane (e.g., paclitaxel or docetaxel) in the amount of 29-31 mg. In further embodiments, the solid dispersion comprises about 30 mg (e.g., 29.5-30.5 mg) taxane.

In some embodiments, the solid dispersion comprises a taxane (e.g., paclitaxel or docetaxel) in the amount of 25-35 mg, a pharmaceutically acceptable polymer (e.g., polyvinylpyrrolidone) in the amount of 60-180 mg, a polysorbate (e.g., polysorbate 80) in the amount of 25-35 mg, and sodium lauryl sulfate in the amount of 0-60 mg. In further embodiments, the solid dispersion comprises a taxane (e.g., paclitaxel or docetaxel) in the amount of 28-32 mg. In further embodiments, the solid dispersion comprises a taxane (e.g., paclitaxel or docetaxel) in the amount of 29-31 mg. In further embodiments, the solid dispersion comprises about 30 mg (e.g., 29.5-30.5 mg) taxane.

In some embodiments, the solid dispersion comprises a taxane (e.g., paclitaxel or docetaxel) in the amount of 25-35 mg, a pharmaceutically acceptable polymer (e.g., polyvinylpyrrolidone) in the amount of 60-180 mg, a polysorbate (e.g., polysorbate 80) in the amount of about 30 mg (e.g., 28-32 mg), and sodium lauryl sulfate in the amount of 0-60 mg. In further embodiments, the solid dispersion comprises a taxane (e.g., paclitaxel or docetaxel) in the amount of 28-32 mg. In further embodiments, the solid dispersion comprises a taxane (e.g., paclitaxel or docetaxel) in the amount of 29-31 mg. In further embodiments, the solid dispersion comprises about 30 mg (e.g., 29.5-30.5 mg) taxane.

In some embodiments, the solid dispersion comprises a taxane (e.g., paclitaxel or docetaxel) in the amount of 25-35 mg, a pharmaceutically acceptable polymer (e.g., polyvinylpyrrolidone) in the amount of 60-180 mg, a polysorbate (e.g., polysorbate 80) in the amount of 0-60 mg, and sodium lauryl sulfate in the amount of 15-45 mg. In further embodiments, the solid dispersion comprises a taxane (e.g., paclitaxel or docetaxel) in the amount of 28-32 mg. In further embodiments, the solid dispersion comprises a taxane (e.g., paclitaxel or docetaxel) in the amount of 29-31 mg. In further embodiments, the solid dispersion comprises about 30 mg (e.g., 29.5-30.5 mg) taxane.

In some embodiments, the solid dispersion comprises a taxane (e.g., paclitaxel or docetaxel) in the amount of 25-35 mg, a pharmaceutically acceptable polymer (e.g., polyvinylpyrrolidone) in the amount of 60-180 mg, a polysorbate (e.g., polysorbate 80) in the amount of 0-60 mg, and sodium lauryl sulfate in the amount of 20-40 mg. In further embodiments, the solid dispersion comprises a taxane (e.g., paclitaxel or docetaxel) in the amount of 28-32 mg. In further embodiments, the solid dispersion comprises a taxane (e.g., paclitaxel or docetaxel) in the amount of 29-31 mg. In further embodiments, the solid dispersion comprises about 30 mg (e.g., 29.5-30.5 mg) taxane.

In some embodiments, the solid dispersion comprises a taxane (e.g., paclitaxel or docetaxel) in the amount of 25-35 mg, a pharmaceutically acceptable polymer (e.g., polyvinylpyrrolidone) in the amount of 60-180 mg, a polysorbate (e.g., polysorbate 80) in the amount of 0-60 mg, and sodium lauryl sulfate in the amount of 25-35 mg. In further embodiments, the solid dispersion comprises a taxane (e.g., paclitaxel or docetaxel) in the amount of 28-32 mg. In further embodiments, the solid dispersion comprises a taxane (e.g., paclitaxel or docetaxel) in the amount of 29-31 mg. In further embodiments, the solid dispersion comprises about 30 mg (e.g., 29.5-30.5 mg) taxane.

In some embodiments, the solid dispersion comprises a taxane (e.g., paclitaxel or docetaxel) in the amount of 25-35 mg, a pharmaceutically acceptable polymer (e.g., polyvinylpyrrolidone) in the amount of 60-180 mg, a polysorbate (e.g., polysorbate 80) in the amount of 0-60 mg, and sodium lauryl sulfate in the amount of about 30 mg (e.g., 28-32 mg). In further embodiments, the solid dispersion comprises a taxane (e.g., paclitaxel or docetaxel) in the amount of 28-32 mg. In further embodiments, the solid dispersion comprises a taxane (e.g., paclitaxel or docetaxel) in the amount of 29-31 mg. In further embodiments, the solid dispersion comprises about 30 mg (e.g., 29.5-30.5 mg) taxane.

In some embodiments, the solid dispersion comprises a taxane (e.g., paclitaxel or docetaxel) in the amount of 25-35 mg, a pharmaceutically acceptable polymer (e.g., polyvinylpyrrolidone) in the amount of 85-100 mg, a polysorbate (e.g., polysorbate 80) in the amount of 25-35 mg, and sodium lauryl sulfate in the amount of 25-35 mg. In further embodiments, the solid dispersion comprises a taxane (e.g., paclitaxel or docetaxel) in the amount of 28-32 mg. In further embodiments, the solid dispersion comprises a taxane (e.g., paclitaxel or docetaxel) in the amount of 29-31 mg. In further embodiments, the solid dispersion comprises about 30 mg (e.g., 29.5-30.5 mg) taxane.

In some embodiments, the solid dispersion comprises a taxane (e.g., paclitaxel or docetaxel) in the amount of 25-35 mg, a pharmaceutically acceptable polymer (e.g., polyvinylpyrrolidone) in the amount of about 90 mg (e.g., 85-95 mg), a polysorbate (e.g., polysorbate 80) in the amount of about 30 mg (e.g., 28-32 mg), and sodium lauryl sulfate in the amount of about 30 mg (e.g., 28-32 mg). In further embodiments, the solid dispersion comprises a taxane (e.g., paclitaxel or docetaxel) in the amount of 28-32 mg. In further embodiments, the solid dispersion comprises a taxane (e.g., paclitaxel or docetaxel) in the amount of 29-31 mg. In further embodiments, the solid dispersion comprises about 30 mg (e.g., 29.5-30.5 mg) taxane.

In some embodiments, the solid dispersion comprises a taxane (e.g., paclitaxel or docetaxel) in the amount of 25-35 mg, a pharmaceutically acceptable polymer (e.g., polyvinylpyrrolidone) in the amount of 90 mg, a polysorbate (e.g., polysorbate 80) in the amount of 30 mg, and sodium lauryl sulfate in the amount of 30 mg. In further embodiments, the solid dispersion comprises a taxane (e.g., paclitaxel or docetaxel) in the amount of 28-32 mg. In further embodiments, the solid dispersion comprises a taxane (e.g., paclitaxel or docetaxel) in the amount of 29-31 mg. In further embodiments, the solid dispersion comprises about 30 mg (e.g., 29.5-30.5 mg) taxane. In further embodiments, the solid dispersion comprises 30 mg taxane.

In some embodiments, the solid dispersion has a total weight of 150-210 mg, 160-200 mg, or 170-190 mg. In further embodiments, the solid dispersion has a total weight of about 180 mg (e.g., 175-185 mg).

The solid dispersion of the present invention possesses various advantageous properties. In some embodiments, the solid dispersion of the present invention has improved storage stability (e.g., at 60° C.). In some embodiments, the solid dispersion of the present invention comprises less than 1%, 0.7%, 0.6%, or 0.5% impurities after 4 weeks of storage at 60° C. In some embodiments, the solid dispersion of the present invention comprises less than 0.2% baccatin III after 4 weeks of storage at 60° C. In some embodiments, the solid dispersion of the present invention comprises less than 0.05%, 0.02%, or 0.01% 10-deacetylpaclitaxel after 4 weeks of storage at 60° C. In some embodiments, the solid dispersion of the present invention comprises less than 0.2%, 0.15% or 0.1% 2-debenzonyl docetaxel-2-pentenoate after 4 weeks of storage at 60° C. In some embodiments, the solid dispersion of the present invention comprises less than 0.005%, 0.002%, or 0.001% 2-debenzonylpaclitaxel-2-pentenoate after 4 weeks of storage at 60° C. In some embodiments, the solid dispersion of the present invention comprises less than 0.005%, 0.002%, or 0.001% 10-deacetyl-7-epipaclitaxel after 4 weeks of storage at 60° C. In some embodiments, the solid dispersion of the present invention comprises less than 0.4% 7-epipaclitaxel after 4 weeks of storage at 60° C.

(4) Method for Preparing the Solid Dispersion

The method of the present application for preparing an amorphous taxane solid dispersion comprises dissolving a taxane in a sufficient amount of an organic solvent, and mixing the resultant solution with a solution containing a pharmaceutically acceptable polymer and a pharmaceutically acceptable surfactant, thereby preparing a spray solution. The solvent may then be evaporated away, leaving the drug dispersed/dissolved in the matrix.

The solid matrix has a taxane finely dispersed (molecular dispersion) in such a way that the dissolution of a taxane is maximized, thus improving the bioavailability of a taxane.

In some embodiments, the method comprises the steps of:
(a) dissolving a taxane or a pharmaceutically acceptable salt thereof, a pharmaceutically acceptable polymer and a pharmaceutically acceptable surfactant in a solvent; and
(b) drying the solution obtained in step (a).

In some embodiments, Step (a) comprises: dissolving a taxane in a sufficient amount of an organic solvent; dissolving a pharmaceutically acceptable polymer and a pharmaceutically acceptable surfactant in a solvent; and mixing the two solution.

In some embodiments, Step (b) comprises spray drying. In further embodiments, Step (b) comprises spray drying in combination with a fluid bed.

In some embodiments, the method may further comprise a step of drying the solid dispersion.

Particularly, the method for the preparation of an amorphous taxane solid dispersion by the spray drying technique of the present invention comprises the following steps:

1. Preparation of the spray solution containing a taxane, a pharmaceutically acceptable polymer and a pharmaceutically acceptable surfactant.
2. Formation of solid dispersion by spraying the solution of Step 1) via a nozzle to obtain a solid dispersion.
3. Collection of the solid dispersion prepared thereby and drying if necessary.

The above steps of the inventive method are each described in detail as follows.

Step 1: Preparation of the Spray Solution Containing a Taxane, a Pharmaceutically Acceptable Polymer and a Pharmaceutically Acceptable Surfactant In Step 1), the spray solution for producing a solid dispersion is prepared by mixing Solution A: an organic solvent solution containing a taxane, and Solution B: an aqueous-organic solvent solution containing a pharmaceutically acceptable polymer and a pharmaceutically acceptable surfactant.

In accordance with the present invention, the organic solvent for dissolving a taxane in Solution A includes, but is not limited to, an alcohol, a haloalkane, ethyl acetate, N,N-dimethylformamide, DMSO, tetrahydrofuran, or a mixture thereof. Preferably, the alcohol is a $C_1$-$C_3$ alcohol, such as methanol, ethanol, propanol or isoprapanol. More preferably, the alcohol is ethanol. Preferably, the haloalkane is a $C_1$-$C_3$ alkane (e.g., methane, ethane or propane) substituted with 1, 2, 3 or 4 halogen. More preferable, the haloalkane is a $C_1$-$C_3$ alkane (e.g., methane, ethane or propane) substituted with 1, 2, 3 or 4 chlorine. More preferably, the haloalkane is dichloromethane, chloroform or carbon tetrachloride.

Further, the organic solvent used in the aqueous-organic solvent for dissolving a pharmaceutically acceptable polymer and a pharmaceutically acceptable surfactant in Solution B includes, but is not limited to, an alcohol, a haloalkane, ethyl acetate, N,N-dimethylformamide, DMSO, or tetrahydrofuran, or a mixture thereof. In some embodiments, the organic solvent in Solution B is the same as the organic solvent in Solution A. In other embodiments, the organic solvent in Solution B is different from the organic solvent in Solution A. Preferably, the organic solvent in Solution B is an alcohol. Preferably, the alcohol is a $C_1$-$C_3$ alcohol, such as methanol, ethanol, propanol or isoprapanol. More preferably, the alcohol is ethanol. Accordingly, the aqueous-organic solvent in Solution B includes, but is not limited to, ethanol/water, methanol/water or isopropanol/water, preferably ethanol/water. Since the above two solvent systems can easily mix with each other, a mixture thereof forms a homogenous solution.

The wt/wt ratio between the organic solvent and water is 20:1 to 1:20, 10:1 to 1:10, 9:1 to 1:9, 8:1 to 1:8, 7:1 to 1:7, 6:1 to 1:6, 5:1 to 1:5, 4:1 to 1:4, 3:1 to 1:3, 2:1 to 1:2, 1.5:1 to 1:1.5, 1.3:1 to 1:1.3, 1.2/1 to 1:1.2, or 1.1:1 to 1:1.1. In some embodiments, the wt/wt ratio is 5:1 to 1:5, 4:1 to 1:4, 3:1 to 1:3, 2:1 to 1:2, 1.5:1 to 1:1.5, 1.3:1 to 1:1.3, 1.2/1 to 1:1.2, or 1.1:1 to 1:1.1. In further embodiments, the wt/wt ratio is 2:1 to 1:2, 1.5:1 to 1:1.5, 1.3:1 to 1:1.3, 1.2/1 to 1:1.2, or 1.1:1 to 1:1.1. In further embodiments, the wt/wt ratio is 1.3:1 to 1:1.3, 1.2/1 to 1:1.2, or 1.1:1 to 1:1.1. In further embodiments, the wt/wt ratio is 1.1:1 to 1:1.1. In further embodiments, the wt/wt ratio is 1:05:1 to 1:1.05. In further embodiments, the wt/wt ratio is about 1:1.

The wt/wt ratio between the organic solvent in Solution A and the aqueous-organic solvent in Solution B is 9:1 to 1:9, 8:2 to 2:8, 7:3 to 3:7, or 6:4 to 4:6. In some embodiments, the wt/wt ratio is 8:2 to 2:8, 7:3 to 3:7, or 6:4 to 4:6. In further embodiments, the wt/wt ratio is 7:3 to 3:7 or 6:4 to 4:6. In further embodiments, the wt/wt ratio is about 4:6.

Solution A and Solution B can be mixed by adding Solution A to Solution B, or by adding Solution B to Solution A. In some embodiments, Solution A is slowly added to Solution B. In other embodiments, Solution B is slowly added to Solution A.

Step 2: Formation of Solid Dispersion by Spraying the Solution Obtained in Step 1

In this step, the solvent may be removed by evaporation by spray drying technique. The term "spray-drying" is used conventionally and broadly refers to processes involving breaking up liquid mixtures into small droplets (atomization) and rapidly removing solvent from the mixture in a spray-drying apparatus where there is a strong driving force for evaporation of solvent from the droplets. In a typical spray drying process, the feed liquid may be a solution, slurry, emulsion, gel or paste, provided it is pumpable and capable of being atomized.

In one embodiment, the process according to the present invention is generally carried out by conventional spray drying technique. Spray-drying processes and spray-drying equipment are described generally in Perry's Chemical Engineers' Handbook, pages 20-54 to 20-57 (Sixth Edition 1984). More details on spray-drying processes and equipment are reviewed by Marshall, "Atomization and Spray-Drying," 50 Chem. Eng. Prog. Monogr. Series 2 (1954), and Masters, Spray Drying Handbook (Fourth Edition 1985). The driving force for solvent elimination or evaporation is usually provided by keeping the partial pressure of solvent in the spray-drying equipment substantially below the vapor pressure of the solvent at the temperature of the drying droplets.

In another embodiment according to the present invention, the process of producing a solid dispersion is a combination of fluid bed technology and spray-drying technology.

In the fluid bed technology, powders comprising the active ingredient are generally suspended in a stream of upwardly moving air while at the same time a controlled and defined amount of liquid is injected into the powder stream to produce a moistened state or "agglomeration" of the powder; mild heat is then used to dry the agglomerated powder. Following this agglomeration, the powder has altered physical characteristics from the starting powder.

In some embodiments, by combining the fluid bed and spray drying technology, solid dispersion particles of poorly water-soluble or substantially water-insoluble compound are produced by finely-spraying a non-aqueous solution of a compound (e.g., a taxane) into a heated and fluidized bed of carrier excipients. The resulting product is a solid dispersion consisting of a free flowing mixture of relatively larger granular particles of carrier excipients and amorphous compound (e.g. a taxane).

In some embodiments, this process comprises a) introducing carrier excipients, into a fluidized bed drier; b) spraying of solution prepared in Step 1) onto the fluidized bed of excipients. In some embodiments, the carrier excipients are in the form of a dry powder when introduced into the fluid bed. In some embodiments, the fluid bed is kept at from about 20° C. to about 80° C., preferably about 25° C. to about 50° C., in particular about 27° C. to about 45° C.

The fluid bed dryer may contain pharmaceutical excipients during the process of spray drying. This enables the drying and formation of solid dispersions on the pharmaceutical excipients inside the fluid bed dryer. The pharmaceutical excipients in accordance with the invention include, but not limited to, fillers, disintegrants, surfactants, adsorbents, and lubricants.

Fillers which are useable in accordance with the invention include, but are not limited to, lactose (anhydrous), lactose monohydrate, spray-dried lactose; compressible sugar, dextrose, dextrates; starches (including starches from any source, such as corn, potato, rice, wheat, which can be fully pregelatinized and partially gelatinized); cellulose; inorganic salts such as calcium phosphate, tribasic calcium and calcium sulfate; and polyols such as mannitol, sorbitol and xylitol.

In some embodiments, microcrystalline cellulose is used in fluid bed of the fluid bed dryer when the solid dispersion solution containing a taxane or its salt thereof is sprayed into the fluid bed.

In some embodiments, the weight ratio of solid dispersion to the filler in the fluid bed may be 1:1 to 1:10. In further embodiments, the weight ratio may be 1:1 to 1:5.

Disintegrants which are useable in accordance with the invention include, but are not limited to, croscarmellose sodium, sodium starch glycolate, starches (including starches from any source, such as corn, potato, rice, wheat, which can be fully pregelatinized and partially gelatinized), crospovidone, alginates such as calcium alginate and sodium alginate, alginic acid, and magnesium aluminum silicate.

In some embodiments, croscarmellose sodium may be used in fluid bed of the fluid bed dryer when the solid dispersion solution containing a taxane or its salt thereof is sprayed into the fluid bed.

In some embodiments, the weight ratio of the solid dispersion to the disintegrant in the fluid bed may be 1:1 to 1:10. In further embodiments, the weight ratio may be 1:1 to 1:5. In further embodiments, the weight ratio may be 1:1 to 1:2, 1:1.5 to 1:1.8, or 1:1.7 to 1:1.8. In further embodiments, the weight ratio may be 1:1.7 to 1:1.8.

In some embodiments, the amount of the disintegrant in the fluid bed may be 250-350 mg, 280-330 mg, or 290-320 mg. In further embodiments, the amount of the disintegrant in the fluid bed may be about 310 mg (e.g., 300-320 mg).

In some embodiments, a combination of microcrystalline cellulose and croscarmellose sodium is used in fluid bed of the fluid bed dryer when the solid dispersion containing a taxane or its salt thereof solution is sprayed into the fluid bed.

In some embodiments, the weight ratio of filler to disintegrant in the fluid bed may be 1:1 to 1:10. In further embodiments, the weight ratio may be 1:2 to 1:5.

Surfactants which are employable in accordance with the present invention include, but not limited to, polysorbates, poloxamers, polyethylene glycols, bile salts, sodium desoxycholate, sodium lauryl sulfate, tocopherol, polyoxyl castor oil, lecithin, lauryl sulfate, Vitamin E, egg yolk phosphatides, docusate sodium, Capryol 90 (propylene glycol monocaprylate), Capryol PGMC (propylene glycol monocaprylate), deoxycholate, and cholesterol. In some embodiments, the surfactant is sodium lauryl sulfate, Labrasol, polysorbate 20, polysorbate 80, PEG-Vitamin E, or mixtures thereof. In further embodiments, the surfactant is sodium lauryl sulfate.

In some embodiments, the weight ratio of the solid dispersion to the surfactant in the fluid bed may be 20:1 to 1:10. In further embodiments, the weight ratio may be 20:1 to 1:5. In further embodiments, the weight ratio may be 20:1 to 1:1. In further embodiments, the weight ratio may be 20:1 to 5:1. In further embodiments, the weight ratio may be 15:1 to 5:1. In further embodiments, the weight ratio may be 15:1 to 10:1. In further embodiments, the weight ratio may be 15:1 to 12:1. In further embodiments, the weight ratio may be about 12:1 (e.g., 13:1 to 11:1).

In some embodiments, the amount of the surfactant in the fluid bed may be 1-100 mg, 2-80 mg, 3-50 mg, 4-40 mg, 5-30 mg, 6-20 mg, or 8-15 mg. In further embodiments, the amount of the surfactant in the fluid bed may be about 14 mg (e.g., 13-15 mg).

Step 3: Collection of Spray Dried Solid Dispersion

Once the spraying is over, the feed and atomization are stopped, and the resultant solid dispersion is collected and dried further if necessary in an oven at 40–60° C., more preferably at 40-50° C.

The result of analyzing the thermochemical properties of the inventive solid dispersion with a differential scanning calorimeter (DSC) shows that while a taxane powder showed a strong endothermic peak at around 220° C., the taxane solid dispersion of the present invention does not show any endothermic peak. Accordingly, it has been confirmed that the collected taxane powder formulation of the present invention is a solid dispersion having an altered molecular arrangement (amorphous or non-crystalline). The resulting solid dispersion can be formulated into pharmaceutical compositions that exhibit high bioavailability.

2. Pharmaceutical Formulation According to the Present Invention

Oral formulations of the present invention are preferably in the form of capsules, tablets, pills, dispersions, solutions, or suspensions. A therapeutically effective oral dosage for formulations of the invention is determined by standard clinical techniques according to the judgment of a medical practitioner. For example, in addition to information provided in medical reference books and pharmaceutical literature, well-known in vitro or in vivo assays can be used to help identify optimal dosages.

In some embodiments, the present invention provides a tablet comprising the amorphous solid dispersion of the present invention, an intragranular excipient, and an extragranular excipient.

The tablet containing the solid dispersion of this invention can be prepared by mixing the amorphous solid dispersion with an intragranular excipient, and an extragranular excipient, and then by compressing the resulting mixture to form a tablet. In the tablet, the amorphous solid dispersion may be employed in an amount of 15 to 50% by weight, based on the total weight of the tablet. In some embodiments, the amorphous solid dispersion is employed in an amount of 20 to 30% by weight, based on total tablet weight. In further embodiments, the amorphous solid dispersion is employed in an amount of about 25% (e.g., 24-28%) by weight, based on total tablet weight.

In addition to the solid dispersion, the tablet of the present invention may further comprise fillers, disintegrants, lubricants, surfactants, or combinations thereof. In some embodiments, the extragranular excipient comprises fillers, disintegrants, lubricants, surfactants, or combinations thereof. In some embodiments, the extragranular excipient comprises fillers, lubricants, or combinations thereof. In some embodiments, the intragranular excipient comprises fillers, disintegrants, lubricants, surfactants, or combinations thereof. In some embodiments, the intragranular excipient comprises disintegrants, surfactants, or combinations thereof.

Fillers which are useable in accordance with the invention include, but are not limited to, lactose (anhydrous), lactose monohydrate, spray-dried lactose; compressible sugar, dextrose, dextrates; starches (including starches from any source, such as corn, potato, rice, wheat, which can be fully pregelatinized and partially gelatinized); cellulose; inorganic salts such as calcium phosphate, tribasic calcium and calcium sulfate; and polyols such as mannitol, sorbitol and xylitol. In some embodiments, the filler is microcrystalline cellulose. In some embodiments, the extragranular excipient comprises microcrystalline cellulose.

In some embodiments, the filler may be in an amount of 10% to 40% by weight based on the total weight of tablet. In further embodiments, the filler may be in an amount of 15% to 35%. In further embodiments, the filler may be in an amount of 20% to 30%. In further embodiments, the filler may be in an amount of about 28% (e.g., 26%-30%).

In some embodiments, the filler may be in an amount of 70-300 mg. In further embodiments, the filler may be in an amount of 100-250 mg. In further embodiments, the filler may be in an amount of 150-230 mg. In further embodiments, the filler may be in an amount of about 210 mg (e.g., 200-220 mg).

Lubricants which are useable according to the invention include, but are not limited to, magnesium stearate, calcium stearate, zinc stearate, stearic acid, sodium stearyl fumarate, hydrogenated vegetable oils, mineral oil, polyethylene glycols, talc, glyceryl behenate, glyceryl monostearate, glyceryl palmitostearate, leucine, and magnesium lauryl sulfate. In some embodiments, the lubricant is sodium stearyl fumarate. In some embodiments, the extragranular excipient comprises sodium stearyl fumarate.

In some embodiments, the lubricant may be in an amount of 0.5% to 2% by weight based on the total weight of tablet. In further embodiments, the lubricant may be in an amount of 0.75% to 1%. In further embodiments, the lubricant may be in an amount of about 0.8% (e.g., 0.72%-0.88% or 0.77%-0.84%).

In some embodiments, the lubricant may be in an amount of 3-15 mg. In further embodiments, the lubricant may be in an amount of 5-7 mg. In further embodiments, the lubricant may be in an amount of about 6 mg (e.g., 5.5-6.5 mg).

Disintegrants which are useable in accordance with the invention include, but are not limited to, croscarmellose sodium, sodium starch glycolate, starches (including starches from any source, such as corn, potato, rice, wheat, fully pregelatinized and partially gelatinized), crospovidone, alginates such as calcium alginate and sodium alginate, alginic acid, and magnesium aluminum silicate. In some embodiments, the disintegrant is croscarmellose sodium. In some embodiments, the intragranular excipient comprises croscarmellose sodium.

In some embodiments, the disintegrant may be in an amount of 30% to 60% by weight based on the total weight of tablet. In further embodiments, the disintegrant may be in an amount of 35% to 50%. In further embodiments, the disintegrant may be in an amount of about 40% (e.g., 38%-44%).

In some embodiments, the disintegrant may be in an amount of 250-350 mg. In further embodiments, the disintegrant may be in an amount of 280-330 mg. In further embodiments, the disintegrant may be in an amount of 290-320 mg. In further embodiments, the disintegrant may be in an amount of about 310 mg (e.g., 300-320 mg).

The surfactants employable as an additive in the present invention include, but are not limited to, polysorbate, poloxamer, sodium lauryl sulfate, tocopherol, lecithin, lauryl sulfate, Vitamin E, egg yolk phosphatides, docusate sodium, Capryol, Labrafil, Labrasol, Lauroglycol, Solutol (Macrogol-15 hydroxystearate), and mixtures thereof. In some embodiments, surfactants include polysorbates, sodium lauryl sulfate, labrasol, and lecithin. In further embodiments, the surfactant is sodium lauryl sulfate. In some embodiments, the intragranular excipient comprises sodium lauryl sulfate.

In some embodiments, the surfactant may be in an amount of 1% to 3%. In further embodiments, the surfactant may be in an amount of 1.5% to 2.5%. In further embodiments, the surfactant may be in an amount of about 1.8% (e.g., 1.7% to 1.9%).

In some embodiments, the surfactant may be in an amount of 4-40 mg. In further embodiments, the surfactant may be in an amount of 5-30 mg. In further embodiments, the surfactant may be in an amount of 6-20 mg. In further embodiments, the surfactant may be in an amount of 8-15 mg. In further embodiments, the surfactant may be in an amount of about 14 mg (e.g., 13-15 mg).

In the method of the present invention, the intragranular excipient may be selected from the group consisting of microcrystalline cellulose, croscarmellose sodium, sodium lauryl sulfate, and a mixture thereof, and the extragranular excipient may be selected from the group consisting of microcrystalline cellulose, croscarmellose sodium, sodium stearyl fumarate, and a mixture thereof. In the method of the present invention, the intragranular excipient may be selected from the group consisting of croscarmellose sodium, sodium lauryl sulfate, and a mixture thereof, and the extragranular excipient may be selected from the group consisting of microcrystalline cellulose, sodium stearyl fumarate, and a mixture thereof.

In some embodiments, the extragranular excipient comprises microcrystalline cellulose and sodium stearyl fumarate. In further embodiments, the extragranular excipient comprises microcrystalline cellulose in an amount of 10% to 40% and sodium stearyl fumarate in an amount of 0.5% to 2% by weight based on the total weight of tablet. In further embodiments, the extragranular excipient comprises microcrystalline cellulose in an amount of 15% to 35% and sodium stearyl fumarate in an amount of 0.75% to 1% by weight based on the total weight of tablet. In further embodiments, the extragranular excipient comprises microcrystalline cellulose in an amount of about 25% and sodium stearyl fumarate in an amount of about 0.8% by weight based on the total weight of tablet.

In some embodiments, the amorphous solid dispersion is in an amount of 15% to 50% by weight, based on the total weight of the tablet. In further embodiments, the amorphous solid dispersion is in an amount of 18% to 40% by weight, based on the total weight of the tablet. In further embodiments, the amorphous solid dispersion is in an amount of 20% to 30% by weight, based on the total weight of the tablet. In further embodiments, the amorphous solid dispersion is in an amount of about 25% (e.g., 23% to 27%) by weight, based on the total weight of the tablet.

In some embodiments, the amorphous solid dispersion in the tablet has a total weight of 150-210 mg, 160-200 mg, or 170-190 mg. In further embodiments, the solid dispersion has a total weight of about 180 mg (e.g., 175-185 mg).

In some embodiments, the extragranular excipient comprises microcrystalline cellulose and sodium stearyl fumarate. In further embodiments, the extragranular excipient comprises microcrystalline cellulose in an amount of 70-300 mg and sodium stearyl fumarate in an amount of 3-15 mg. In further embodiments, the extragranular excipient comprises microcrystalline cellulose in an amount of 100-250 mg and sodium stearyl fumarate in an amount of 5-7 mg. In further embodiments, the extragranular excipient comprises microcrystalline cellulose in an amount of 150-230 mg and sodium stearyl fumarate in an amount of 5-7 mg. In further embodiments, the extragranular excipient comprises microcrystalline cellulose in an amount of about 210 mg and sodium stearyl fumarate in an amount of about 6 mg.

In some embodiments, the intragranular excipient comprises croscarmellose sodium and sodium lauryl sulfate. In further embodiments, the intragranular excipient comprises croscarmellose sodium in an amount of 30% to 60% and sodium lauryl sulfate in an amount of 1% to 3% by weight based on the total weight of tablet. In further embodiments, the intragranular excipient comprises croscarmellose sodium in an amount of 35% to 50% and sodium lauryl sulfate in an amount of 1.5% to 2.5% by weight based on the total weight of tablet. In further embodiments, the intragranular excipient comprises croscarmellose sodium in an amount of about 40% and sodium lauryl sulfate in an amount of about 1.8% by weight based on the total weight of tablet.

In some embodiments, the intragranular excipient comprises croscarmellose sodium and sodium lauryl sulfate. In further embodiments, the intragranular excipient comprises croscarmellose sodium in an amount of 250-350 mg and sodium lauryl sulfate in an amount of 4-40 mg. In further embodiments, the intragranular excipient comprises croscarmellose sodium in an amount of 280-330 mg and sodium lauryl sulfate in an amount of 5-30 mg. In further embodiments, the intragranular excipient comprises croscarmellose sodium in an amount of 290-320 mg and sodium lauryl sulfate in an amount of 6-20 mg. In further embodiments, the intragranular excipient comprises croscarmellose sodium in an amount of about 310 mg and sodium lauryl sulfate in an amount of about 14 mg.

In some embodiments, the tablet of the present invention may further comprise a weak acid. Weak acids employable as an additive in the tablet include, but are not limited to, citric acid, ascorbic acid, acetic acid, and lactic acid. In some embodiments, the weak acid is citric acid or ascorbic acid, or a mixture thereof. In some embodiments, the weak acid is a mixture of citric acid and ascorbic acid. In further embodiments, the ratio between citric acid and ascorbic acid is 0:1 to 1:0. In further embodiments, the ratio is about 1:1.

In some embodiments, the oral formulation of the present invention may further comprise a coating agent such as sugar-based coating agents, water-soluble film coating agents, enteric coating agents and delayed release coating agents or a coating composition comprising any combination thereof. In some embodiments, the coating agent can be any coating agent known in the art. Examples of coating agents include, but are not limited to, saccharose used alone or together with any of the agents such as talc, calcium carbonate, calcium phosphate, calcium sulphate, gelatine, gum arabic, polyvinylpyrrolidone and pullulan or any combination thereof; cellulose derivatives such as hydroxypropyl cellulose, hydroxypropyl methyl cellulose, hydroxyethyl cellulose, methyl hydroxyethyl cellulose and sodium carboxymethyl cellulose; synthetic polymers such as polyvinyl acetal diethyl amino acetate, aminoalkyl methacrylate copolymers and polyvinylpyrrolidone; polysaccharides such as pullulan; hydroxypropyl methyl cellulose phthalate; hydroxypropyl methyl cellulose acetate succinate; carboxymethyl ethyl cellulose; cellulose acetate phthalate; acrylic acid derivatives such as methacrylic acid copolymer L, methacrylic acid copolymer LD and methacrylic acid copolymer S; natural substances such as shellac; titanium dioxide; polyvinyl alcohol (e.g., Opadry®); polyethylene glycol; talc; lecithin; and/or combinations thereof. In one embodiment, the coating agent is selected from hydroxypropyl cellulose, hydroxypropyl methyl cellulose, hydroxyethyl cellulose, methyl hydroxyethyl cellulose, sodium carboxymethyl cellulose, polyvinyl acetal diethyl amino acetate, polyvinyl alcohol, polyethylene glycol, and lecithin, or a combination thereof. In further embodiments, the coating agent is Opadry®.

In some embodiments, the coating agent may be in an amount of 1% to 5%. In further embodiments, the coating agent may be in an amount of 1.5% to 3.5% by weight based on the total weight of tablet. In further embodiments, the coating agent may be in an amount of about 2.8% (e.g., 2.6% to 3.0%).

In some embodiments, the coating agent may be in an amount of 10-50 mg. In further embodiments, the coating agent may be in an amount of 15-40 mg. In further embodiments, the coating agent may be in an amount of 18-30 mg. In further embodiments, the coating agent may be in an amount of 18-25 mg. In further embodiments, the coating agent may be in an amount of about 21 mg (e.g., 19-23 mg).

In some embodiments, the tablet of the present invention comprises a solid taxane dispersion as disclosed herein, an intragranular excipient as disclosed herein, and an extragranular excipient as disclosed herein.

In some embodiments, the tablet of the present invention comprises (1) a solid taxane dispersion comprising a taxane (e.g., paclitaxel or docetaxel) in the amount of about 30 mg, a pharmaceutically acceptable polymer (e.g., polyvinylpyrrolidone) in the amount of about 90 mg, a polysorbate (e.g., polysorbate 80) in the amount of about 30 mg, and sodium lauryl sulfate in the amount of about 30 mg, (2) an intragranular excipient comprising croscarmellose sodium in an amount of about 310 mg and sodium lauryl sulfate in an amount of about 14 mg, and (3) and extragranular excipient comprising microcrystalline cellulose in an amount of about 210 mg and sodium stearyl fumarate in an amount of about 6 mg.

In some embodiments, a tablet comprising the amorphous solid dispersion of a taxane of the present invention can be prepared by the method which comprises the steps of:

(a) dissolving a taxane or a pharmaceutically acceptable salt thereof, a pharmaceutically acceptable polymer and a pharmaceutically acceptable surfactant in a solvent, to produce a solution, and then removing the solvent from the solution to produce a solid dispersion;

(b) mixing together the solid dispersion in Step (a), an intragranular excipient, and an extragranular excipient; and (c) compressing the mixture in Step (b) to form a tablet.

In some embodiments, Step (a) comprises: dissolving a taxane in a sufficient amount of an organic solvent; dissolving a pharmaceutically acceptable polymer and a pharmaceutically acceptable surfactant in a solvent; and mixing the two solution.

In some embodiments, Step (a) comprises spray drying. In further embodiments, Step (a) comprises spray drying in combination with a fluid bed. In further embodiments, the fluid bed comprises the intragranular excipient.

In some embodiments, a tablet comprising the amorphous solid dispersion of a taxane of the present invention can be prepared by the method which comprises the steps of:

(a) dissolving a taxane or a pharmaceutically acceptable salt thereof, pharmaceutically acceptable polymer and a pharmaceutically acceptable surfactant in a solvent, to produce a solution, and then removing the solvent from the solution to produce a solid dispersion;

(b) mixing together the solid dispersion in Step (a) with an intragranular excipient;

(c) mixing together the mixture in Step (b) with an extragranular excipient; and (d) compressing the mixture in Step (c) to form a tablet.

In some embodiments, Step (a) comprises: dissolving a taxane in a sufficient amount of an organic solvent; dissolving a pharmaceutically acceptable polymer and a pharmaceutically acceptable surfactant in a solvent; and mixing the two solution.

In some embodiments, the solid dispersion is mixed with the intragranular excipient in a fluid bed. In some embodiments, the intragranular excipient is added to the fluid bed before being mixed with the solid dispersion. In some embodiments, the intragranular excipient is added to the fluid bed when the spray solution in Step (a) is sprayed into a fluid bed.

In some embodiments, a tablet comprising the amorphous solid dispersion of a taxane of the present invention can be prepared by the method which comprises the steps of:

(a) dissolving a taxane or a pharmaceutically acceptable salt thereof, a pharmaceutically acceptable polymer and a pharmaceutically acceptable surfactant in a solvent, to produce a solution, and then removing the solvent from the solution, for example, by evaporation using the fluid bed spray drying technology, wherein the fluid bed comprises an intragranular excipient, to produce a solid dispersion;

(b) mixing together the solid dispersion with an extragranular excipient; and (c) compressing the resulting mixture to form a tablet.

Tablets, one example of solid oral dosage forms, particularly useful in the practice of the present invention include those selected from the group consisting of IR tablets, CR tablets, SR tablets, coated IR tablets, matrix tablets, coated matrix tablets, multilayer tablets, coated multilayer tablets, multilayer matrix tablets and coated multilayer matrix tablets.

A preferred solid oral dosage form is an immediate release dosage form, which disintegrates immediately in the stomach cavity, and releases the drug and excipients in the gastric region for enhanced absorption by the intestinal cells. A preferred tablet dosage form is a film coated tablet dosage form.

The tablet of the present invention may be film-coated with a coating agent. Examples of the coating agent are hydroxypropyl methyl cellulose, ethyl cellulose, etc. The coating agent may contain, for example, an opaquing agent such as titanium oxide or a plasticizer such as polyethylene glycol.

3. Method of Administration According to the Present Invention

A method for administering a taxane to a subject in need thereof is provided, comprising: providing a pharmaceutical oral solid dosage formulation comprising: a taxane or a pharmaceutically acceptable salt thereof, a pharmaceutically acceptable polymer and a pharmaceutically acceptable surfactant prepared as a solid dispersion, and administering the pharmaceutical formulation in a therapeutically effective amount to a subject in need thereof.

The method may be used for administering a taxane orally to patients with a cell proliferative disease such as cancer including, but not limited to, human ovarian cancer, breast cancer, malignant lymphoma, lung cancer, melanoma, and Kaposi's sarcoma.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the invention encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. Preferably, the methods provided herein are used to treat or alleviate a symptom of cancer. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary non-cancerous conditions or disorders include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A taxane is administered alone or in combination with other therapeutic agents which can act synergistically with a taxane.

In further embodiments, the invention encompasses methods of orally administering a tablet comprising the amorphous solid dispersion containing a taxane, and an additional therapeutic agent. In a further embodiment, the invention encompasses methods of orally administering a tablet comprising the amorphous solid dispersion containing a taxane to a patient in need thereof, an additional therapeutic agent, and a p-glycoprotein inhibitor.

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). In one embodiment, the subject is human. In one embodiment, the subject is human child (e.g., between about 30 kg to about 70 kg). In one embodiment, the human child has had a Kasai procedure, where the Kasai procedure effectively gives them a functional bile duct when they born either without a bile duct or a bile duct completely blocked at birth.

As used herein, the term "about" or "approximately", or the like, means that the value to which it refers to may vary to some extent. For example, the value may vary by 10%, 5%, 2%, or 1%. In some embodiments, the value may vary by 5%, 2%, or 1%. For example, "about 5" is meant to include any value between 4.5 and 5.5, or between 4.75 and 5.25, or between 4.9 and 5.1, or between 4.95 and 5.05.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Treating", includes any effect, e.g., lessening, reducing, modulating, or eliminating, that results in the improvement of the condition, disease, disorder, etc. "Treating" or "treatment" of a disease state includes: inhibiting the disease state, i.e., arresting the development of the disease state or its clinical symptoms; or relieving the disease state, i.e., causing temporary or permanent regression of the disease state or its clinical symptoms.

The term "effective amount" as used herein refers to an amount of obeticholic acid (e.g., an FXR-activating ligand) that produces an acute or chronic therapeutic effect upon appropriate dose administration. The effect includes the prevention, correction, inhibition, or reversal of the symptoms, signs and underlying pathology of a disease/condition (e.g., fibrosis of the liver, kidney, or intestine) and related complications to any detectable extent.

"A therapeutically effective amount" means the amount of obeticholic acid that, when administered to a mammal for treating a disease, is sufficient to effect such treatment for the disease. The "therapeutically effective amount" will vary depending on obeticholic acid, the disease and its severity and the age, weight, etc., of the mammal to be treated.

The therapeutically effective amount can be estimated initially either in cell culture assays or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between toxic and therapeutic effects is the therapeutic index, and it can be expressed as the ratio, LD50/ED50. Pharmaceutical compositions that exhibit large therapeutic indices are preferred. The dosage may vary within this range depending upon the dosage form employed, sensitivity of the patient, and the route of administration.

All publications and patent documents cited herein are incorporated herein by reference as if each such publication or document was specifically and individually indicated to be incorporated herein by reference. Citation of publications and patent documents, is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

In the specification, the singular forms also include the plural, unless the context clearly dictates otherwise. Unless defined otherwise, all technical and scientific terms used herein have the same meaning as commonly understood by one of ordinary skill in the art to which this invention belongs. In the case of conflict, the present specification will control.

All percentages and ratios used herein, unless otherwise indicated, are by weight.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended. It is to be further understood that resort may be had to various other embodiments, modifications, and equivalents thereof which may suggest themselves to those skilled in the art without departing from the spirit of the present disclosure and/or scope of the appended claims.

Examples 1 and 2: Preparation of Solid Dispersions with Different Types of Polymer The solid dispersions of Examples 1 and 2 presented in Table 1 were prepared by the traditional spray drying method using a traditional spray dryer. Two different polymers, HPMC and PVP, were used to prepare the paclitaxel solid dispersions.

Spray drying was performed on a Buchi Mini Spray Dryer. The feed material was atomized through nozzle with the following spray drying conditions: inlet temperature of 65° C., outlet temperature of 45° C., atomization pressure of 0.5 bar, and atomization flow rate of 10% with 80% aspiration. All solutions were prepared at 10% total solids in 3:2 (w:w) Ethanol:Water. Spray dried samples were then dried in a vacuum oven for at least 2 hrs at 50° C.

TABLE 1

| Ingredients (mg) | Example 1 | Example 2 |
|---|---|---|
| Paclitaxel | 30 | 30 |
| HPMC2910 | 150 | — |
| PVP-K30 | — | 150 |
| Sodium lauryl sulfate | 30 | 30 |
| Cremophor EL | 30 | 30 |
| EtOH | 2100 | 2100 |
| Water | 900 | 900 |
| Total | 240 | 240 |

Examples 3 to 6: Preparation of Solid Dispersions with Different Types of Surfactants The solid dispersions of Examples 3 to 6 as presented in Table 2 were prepared using the above-mentioned traditional spray drying method. Various types of surfactants were used to prepare the paclitaxel solid dispersions.

TABLE 2

| Ingredients (mg) | Example 3 | Example 4 | Example 5 | Example 6 |
|---|---|---|---|---|
| Paclitaxel | 30 | 30 | 30 | 30 |
| PVP-K30 | 150 | 150 | 150 | 150 |
| Sodium lauryl sulfate | 30 | 30 | 30 | 30 |
| Cremophor EL | 30 | — | — | — |
| Tween 80 | — | 30 | — | — |
| Labrasol | — | — | 30 | — |
| EtOH | (2100) | (2100) | (2100) | (2100) |
| Water | (900) | (900) | (900) | (900) |
| Total | 240 | 240 | 240 | 210 |

Examples 7 to 10: Preparation of Solid Dispersions with Different Amounts of Polymer The solid dispersions of Examples 7 to 10 as presented in Table 3 were prepared using the above-mentioned traditional spray drying method. Various amounts of polymer were used to prepare the paclitaxel solid dispersions.

TABLE 3

| Ingredients (mg) | Example 7 | Example 8 | Example 9 | Example 10 |
|---|---|---|---|---|
| Paclitaxel | 30 | 30 | 30 | 30 |
| PVP-K30 | 270 | 180 | 90 | 30 |
| Sodium lauryl sulfate | 30 | 30 | 30 | 30 |
| Tween 80 | 30 | 30 | 30 | 30 |
| EtOH | (2100) | (2100) | (2100) | (2100) |
| Water | (900) | (900) | (900) | (900) |
| Total | 360 | 270 | 180 | 120 |
| Paclitaxel:PVP-K30 Ratio | 1:9 | 1:6 | 1:3 | 1:1 |

Example 11: Preparation of Solid Dispersion by Spray Drying Technology

The solid dispersion of Example 11 as presented in Table 4 was prepared using the traditional spray drying method as mentioned in Example 1. The final solid dispersion contained 30 mg equivalent paclitaxel per 210 mg of powder mixture.

TABLE 4

| Ingredients (mg) | Example 11 |
|---|---|
| Paclitaxel | 30 |
| PVP-K30 | 90 |
| Sodium lauryl sulfate | 30 |
| Tween 80 | 60 |
| EtOH | (2100) |
| Water | (900) |
| Total | 210 |

Example 12: Preparation of Solid Dispersion by Fluid Bed Technology

<Example 12-1> Preparation of Solid Dispersion Containing Paclitaxel

The solid dispersion of Example 12-1 as presented in Table 5 was prepared using the fluid bed spray drying technology. Spray solution was prepared by dissolving paclitaxel, PVP-K30, polysorbate 80 and sodium lauryl sulfate in ethanol/water solvent system. The solution was sprayed into 434 g mixture of excipients as shown in Table 5 in fluid bed system. The spray rate was 15-25 mL/min using one top gun. The static inlet pressure was 2.5-5 bar (250-500 kPa). The inlet temperature was 65~70° C. and the product temperature was 30-40° C. The resulting paclitaxel powder mixture was free-flowing and contained 30 mg paclitaxel per 644 mg of final mixture.

TABLE 5

| Ingredients (mg) | Example 12-1 |
|---|---|
| Paclitaxel | 30 |
| PVP-K30 | 90 |
| Sodium lauryl sulfate | 30 |
| Tween 80 | 60 |
| EtOH | (2100) |
| Water | (900) |
| Subtotal | 210 |
| Avicel PH101 | 210 |
| Cross CMC Na | 210 |
| Sodium lauryl sulfate | 14 |
| Total | 644 |

<Examples 12-2 to 12-4> Preparation of Solid Dispersion Containing Different Types of Taxanes The solid dispersions of Examples 12-2 to 12-4 containing taxanes other than paclitaxel as presented in Table 6 were prepared using the fluid bed spray drying technology. Spray solution was prepared by dissolving docetaxel (cabazitaxel, or tesetaxel), PVP-K30, polysorbate 80 and sodium lauryl sulfate in ethanol/water solvent system. The solution was sprayed into 434 g mixture of excipients as shown in Table 6 in fluid bed system. The spray rate was 15~25 mL/min using one top gun. The static inlet pressure was 2.5-5 bar (250-500 kPa). The inlet temperature was 65~70° C. and the product temperature was 30-40° C. The resulting taxane powder mixture was free-flowing and contained 30 mg taxane per 644 mg of final mixture.

TABLE 6

| Ingredients (mg) | Example 12-2 | Example 12-3 | Example 12-4 |
|---|---|---|---|
| Docetaxel | 30 | | |
| Cabazitaxel | | 30 | |
| Tesetaxel | | | 30 |
| PVP-K30 | 90 | 90 | 90 |
| Sodium lauryl sulfate | 30 | 30 | 30 |
| Tween 80 | 60 | 60 | 60 |
| EtOH | (2100) | (2100) | (2100) |
| Water | (900) | (900) | (900) |
| Subtotal | 210 | 210 | 210 |
| Avicel PH101 | 210 | 210 | 210 |
| Cross CMC Na | 210 | 210 | 210 |
| Sodium lauryl sulfate | 14 | 14 | 14 |
| Total | 644 | 644 | 644 |

Comparative Example 1: Preparation of Liquid Formulation Containing Paclitaxel The liquid formulation containing paclitaxel was prepared using the ingredients shown in Table 7. Specifically, paclitaxel as an active ingredient was completely dissolved in Tween 80 as a surfactant using a magnetic stirrer bar.

TABLE 7

| Ingredients (mg) | Comp. Ex. 1 |
|---|---|
| Paclitaxel | 30 |
| Tween 80 | 350 |
| Total | 380 |

Example 13: Preparation of Tablet Containing the Solid Dispersion of Example 11

The tablet was prepared using the solid dispersion of Example 11, as shown in Table 8.

Once the spray drying is over, the solid dispersion of Example 11 was mixed with the intragranular excipients and part of the lubricant was added to the granule mixture and tablets were produced for the slugging process with a hardness of less than 2 kp. The slug was then passed through sieve #20. Remaining amount of lubricant and extragranular excipients were then added to this slug and mixed well, and the final tablets were made by the tablet machine. The tablets prepared were oblong with a thickness of around 6.90 mm, diameter of around 15.83 mm, and a hardness of around 2~5 kp.

TABLE 8

| Ingredients (mg) | Example 13 |
|---|---|
| Solid dispersion of Example 11 | 210 |
| Microcrystalline cellulose | 210 |
| Croscarmellose sodium | 310 |
| Sodium lauryl sulfate | 14 |
| Sodium stearyl fumarate | 6 |
| Total | 750 |

Example 14: Preparation of Tablet Containing the Solid Dispersion of Example 12

<Example 14-1> Preparation Tablet Containing the Solid Dispersion of Example 12-1

The tablet was prepared using the solid dispersion of Example 12-1, as shown in Table 9.

Once the fluid bed process is over, part of the lubricant was added to the granule mixture and tablets were produced for the slugging process with a hardness of less than 2 kp. The slug was then passed through sieve #20. Remaining amount of lubricant was then added to this slug and mixed well, and the final tablets were made by the tablet machine. The tablets prepared were oblong with a thickness of around 6.90 mm, diameter of around 15.83 mm, and a hardness of around 2-5 kp.

TABLE 9

| Ingredients (mg) | Example 14-1 |
| --- | --- |
| Solid dispersion of Example 12-1 | 210 |
| Microcrystalline cellulose | 210 |
| Croscarmellose sodium | 310 |
| Sodium lauryl sulfate | 14 |
| Sodium stearyl fumarate | 6 |
| Total | 750 |

<Examples 14-2 to 14-4> Preparation of Tablet Containing the Solid Dispersion of Examples 12-2 to 12-4

The tablets were prepared using the solid dispersions of Examples 12-2 to 12-4, as shown in Table 10.

Once the fluid bed process is over, part of the lubricant was added to the granule mixture and tablets were produced for the slugging process with a hardness of less than 2 kp. The slug was then passed through sieve #20. Remaining amount of lubricant was then added to this slug and mixed well, and the final tablets were made by the tablet machine. The tablets prepared were oblong with a thickness of around 6.90 mm, diameter of around 15.83 mm, and a hardness of around 2-5 kp.

TABLE 10

| Ingredients (mg) | Example 14-2 | Example 14-3 | Example 14-4 |
| --- | --- | --- | --- |
| Solid dispersion of Example 12-2 | 210 | | |
| Solid dispersion of Example 12-3 | | 210 | |
| Solid dispersion of Example 12-4 | | | 210 |
| Microcrystalline cellulose | 210 | 210 | 210 |
| Croscarmellose sodium | 310 | 310 | 310 |
| Sodium lauryl sulfate | 14 | 14 | 14 |
| Sodium stearyl fumarate | 6 | 6 | 6 |
| Total | 750 | 750 | 750 |

Comparative Example 2: Preparation of Tablet Containing the Solid Dispersion of Paclitaxel by Fluid Bed Spray Drying Technology with Paclitaxel:Polymer Ratio of 1:9 with SLS Only The tablet of Comparative Example 2 as presented in Table 11 was prepared using the fluid bed spray drying technology as mentioned in Example 12-1. Spray solution was prepared by dissolving paclitaxel, sodium lauryl sulfate, and PVP K-30 in ethanol/water solvent system. The solution was sprayed into 300 g mixture of excipients (Microcrystalline cellulose, croscarmellose sodium, and sodium lauryl sulfate) as showed in Table 11, in the fluid bed system. The spray rate was 1525 mL/min using one top gun. The static inlet pressure was 2.5~5 bar (250~500 kPa). The inlet temperature was 65~70° C. and the product temperature was 30~40° C. The resulting granules were free-flowing containing amorphous paclitaxel coated on to the excipients' surface. The resulting paclitaxel granules were free-flowing and contained 30 mg equivalent paclitaxel.

Once the fluid bed process is over, part of the lubricant was added to the granule mixture and tablets were produced for the slugging process with a hardness of less than 2 kp. The slug was then passed through sieve #20. Remaining amount of lubricant was then added to this slug and mixed well, and the final tablets were made by the tablet machine. The tablets prepared were oblong with a thickness of around 6.90 mm, diameter of around 15.83 mm, and a hardness of around 2~5 kp.

TABLE 11

| Ingredients (mg) | Comp. Ex. 2 |
| --- | --- |
| Paclitaxel | 30 |
| PVP-K30 | 270 |
| Sodium lauryl sulfate | 30 |
| Ethanol | (2100) |
| Water | (900) |
| Subtotal | 330 |
| Microcrystalline cellulose | 210 |
| Croscarmellose sodium | 310 |
| Sodium lauryl sulfate | 14 |
| Total | 744 |
| Sodium stearyl fumarate | 6 |
| Total | 870 |

Comparative Example 3: Preparation of Conventional Tablet of Paclitaxel

The conventional tablet containing paclitaxel was prepared using the ingredients shown in Table 12.

First, paclitaxel was mixed with PVP K-30, sodium lauryl sulfate, and Polysorbate 80 (Tween 80) as intragranular excipients and wet granulated to form granules. After drying the granules, microcrystalline cellulose, croscarmellose sodium, and sodium lauryl sulfate and sodium stearyl fumarate as extragranular excipients were mixed, and the final tablets were made by the tablet machine. The tablets prepared were oblong with a thickness of around 6.90 mm, diameter of around 15.83 mm, and a hardness of around 2~5 kp.

TABLE 12

| Ingredients (mg) | Comp. Ex. 3 |
| --- | --- |
| Paclitaxel | 30 |
| PVP-K30 | 90 |
| Sodium lauryl sulfate | 30 |
| Polysorbate 80 (Tween 80) | 60 |
| Microcrystalline cellulose | 210 |
| Croscarmellose sodium | 310 |
| Sodium lauryl sulfate | 14 |
| Sodium stearyl fumarate | 6 |
| Total | 750 |

Test Example 1: Solubility Study of Solid Dispersions of Examples 1 and 2

The solubilities of the solid dispersions of Examples 1 and 2 were investigated using USP XXIII, dissolution apparatus II with 300 mL of pH 1.2 buffer as dissolution medium at 37±0.5° C. with paddle speed of 50 rpm. The solid dispersions of paclitaxel (90 mg as of paclitaxel) were introduced into dissolution tester (Labfine, Korea). At predetermined time intervals, an aliquot of 5 mL was collected, filtered, and analyzed for the content of paclitaxel by the HPLC method. An equivalent volume (5 mL) of fresh dissolution medium was replaced to compensate the loss due to sampling, and the sink condition was maintained throughout the study. The theoretical concentration of paclitaxel in the medium is 300 PPM (90 mg paclitaxel in 300 mL medium). The results are shown in FIG. 1.

As shown in FIG. 1, the solubility of the solid dispersion of Example 2 containing PVP polymer was better than that of the solid dispersion of Example 1. Also, the solubility of the solid dispersion of Example 2 containing PVP was higher and faster, which was chosen for further development.

Test Example 2: Solubility Study of Solid Dispersions of Examples 3 to 6

The solubilities of the solid dispersions of Examples 3 to 6 were investigated using the same conditions discussed in Test Example 1. The effects of various types of surfactants on the solubility of paclitaxel in addition to SLS were shown in FIG. 2.

Figure 2:
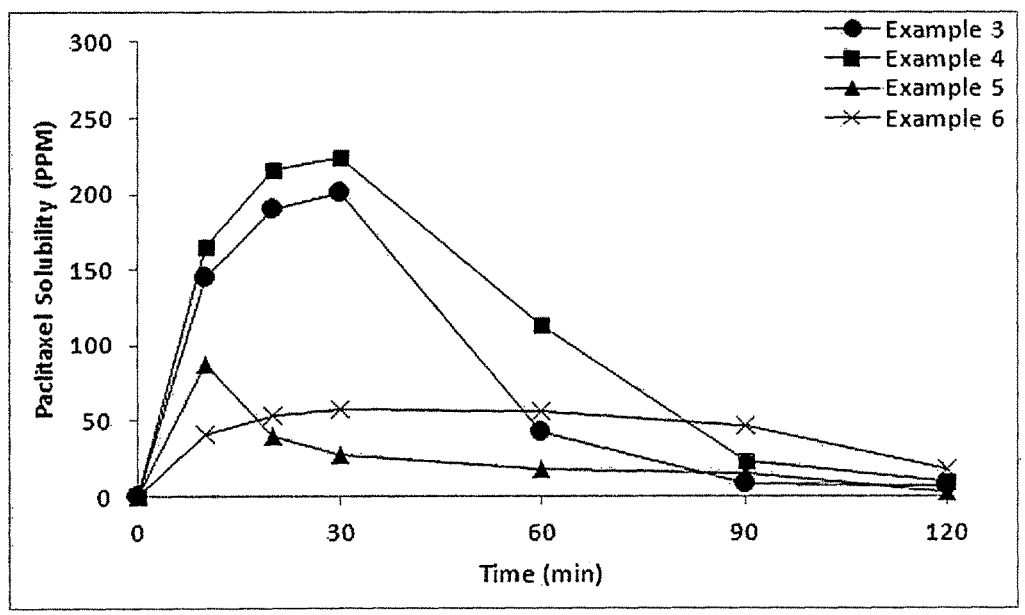
FIG. 2 is a graph showing the solubilities of the solid dispersions of Examples 3 to 6.

As can be seen in FIG. 2, it was clear that the solid dispersion of Example 4 containing Tween 80 and SLS as the surfactants showed highest solubility among the tested dispersions. The solid dispersion of Example 5 containing Labrasol and SLS only showed poor solubility of paclitaxel in the dissolution medium. The solid dispersion of Example 6 containing only SLS without additional surfactants exhibited the poorest solubility among the tested dispersions at paclitaxel dose of 30 mg. The solid dispersion of Example 3 containing Cremophor EL showed the second highest solubility. However, given that the Cremophor is toxic and one of the objectives of the invention is to prepare formulations without Cremophor, the use of surfactant Tween 80 in the preparation of solid dispersion was believed to be highly appropriate.

Test Example 3: Solubility Study of Solid Dispersions of Examples 7 to 10

Figure 3:
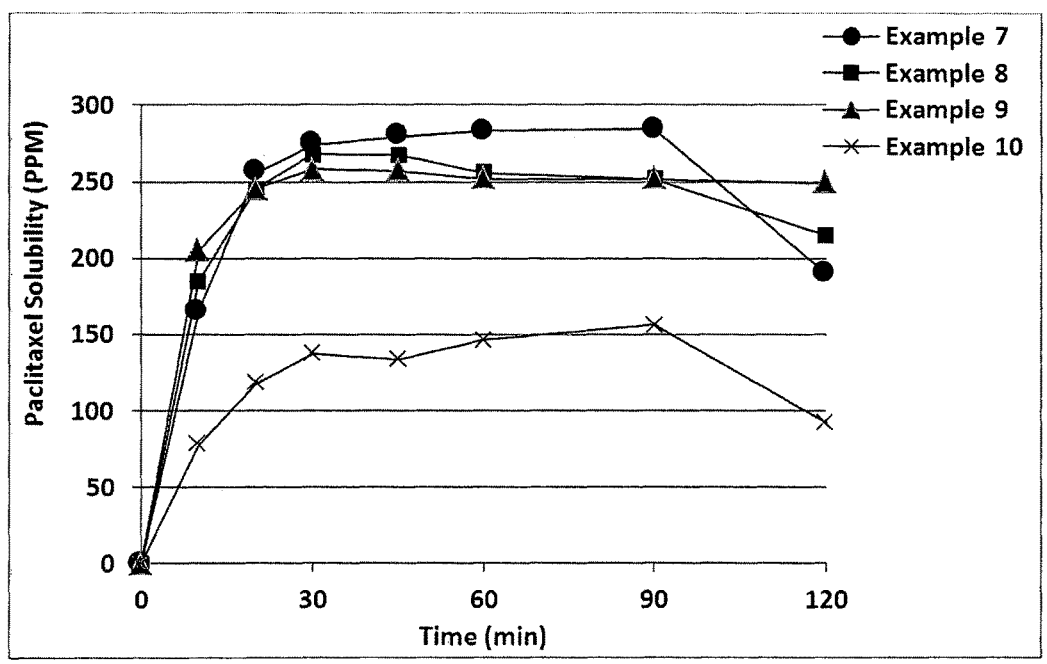
FIG. 3 is a graph showing the solubilities of the solid dispersions of Examples 7 to 10.

The solubilities of the solid dispersions of Example 7 to 10 were investigated using the same conditions discussed in Test Example 1. The effect of the amount of polymer on the solubility of paclitaxel was investigated in this study. The amount of PVP K30 polymer ranging of 30~270 mg was used to prepare the solid dispersions. The results are shown in FIG. 3. The weight ratio of paclitaxel to PVP K-30 used were 1:9 (30:270), 1:6 (30:180), 1:3 (30:90), and 1:1 (30:30).

There was no significant difference between Examples 7, 8 and 9, containing 270, 180 mg, and 90 mg of polymer, respectively, corresponding to a ratio of 1:9, 1:6, and 1:3, respectively. However, the paclitaxel precipitated earlier at 90 min when the polymer amount was more than 90 mg, while the solubility was stable with 90 mg of polymer (ratio 1:3). The solid dispersion of Example 10 containing a low amount of polymer (30 mg) showed poor solubility of paclitaxel suggesting poor carrier effect of polymer at this amount range.

Besides, it is known scientific fact that increasing polymer amount would increase the disintegration and dissolution of compressed tablets due to increased time for hydration leading to sustained effects. Considering this factor, use of minimal amount of polymer is advised and the ratio of 1:3 is considered better in terms of prevention of precipitation, decreased disintegration time, and faster dissolution.

Test Example 4: Solubility Test of Solid Dispersions of Example 11 and 12-1, and Comparative Example 1

The solubilities of the solid dispersions of Examples 11 and 12-1 were investigated using USP XXIII, dissolution apparatus II with 300 mL of pH 1.2 buffer as dissolution medium at 37±0.5° C. with paddle speed of 50 rpm. For comparison, the liquid formulation of Comparative Example 1 (equivalent to 90 mg of paclitaxel) was also added directly into the dissolution medium.

The solid dispersions of paclitaxel (90 mg as of paclitaxel) were introduced into dissolution tester (Labfine, Korea). At predetermined time intervals, an aliquot of 5 mL was collected, filtered, and analyzed for the content of paclitaxel by the HPLC method. An equivalent volume (5 mL) of fresh dissolution medium was replaced to compensate the loss due to sampling, and the sink condition was maintained throughout the study. The theoretical concentration of paclitaxel in the medium is 300 PPM (90 mg paclitaxel in 300 mL medium).

Figure 4:
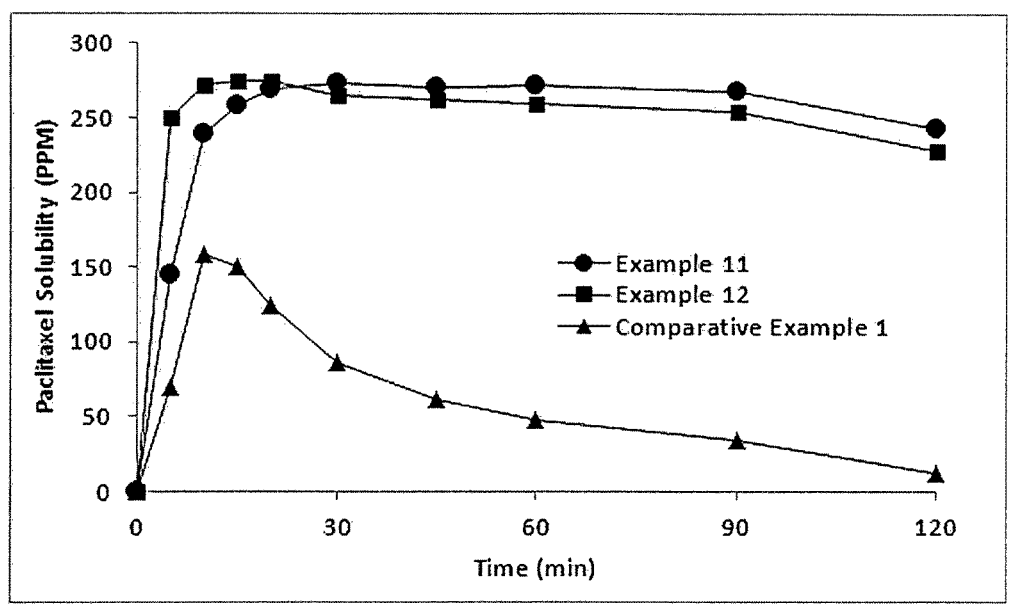
FIG. 4 is a graph showing the solubilities of the solid dispersions of Examples 11 and 12-1, and the liquid formulation of Comparative Example 1.

The solubility profiles of the solid dispersions of Examples 11 and 12-1, and the liquid formulation of Comparative Example 1 were shown in FIG. 4. The solubility of the solid dispersion of Example 12-1 prepared by fluid bed technology showed the fastest dissolution among the samples tested. The liquid formulation of Comparative Example 1 showed poor solubility and faster recrystallization compared to the solid dispersions. According to FIG. 4, it could be understood that amorphous solid dispersions prepared by either traditional or fluid bed technique was superior than even the liquid formulation, and this composition and process of preparation could be considered as excellent method for increasing solubility of paclitaxel.

Test Example 5: Solubility Study of Tablets of Examples 13 and 14-1, and Comparative Example 2

Figure 5:
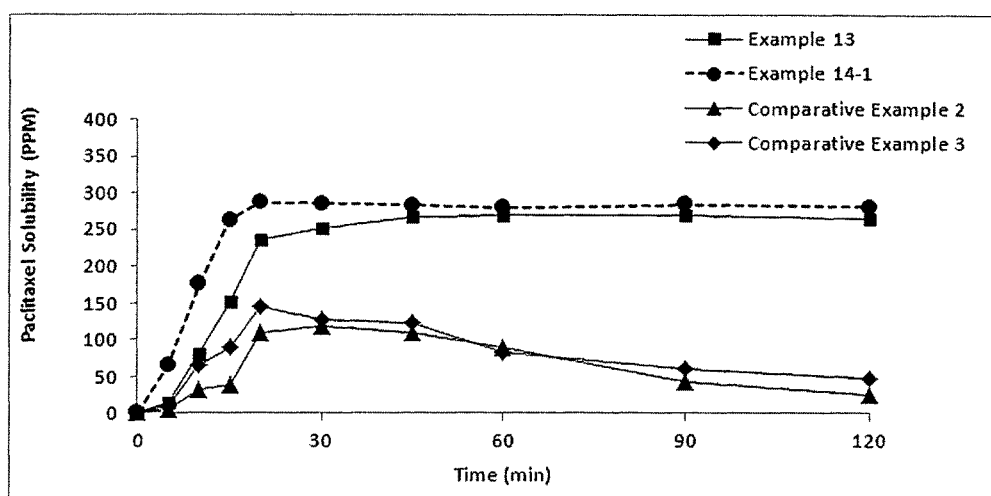
FIG. 5 is a graph showing the disintegration of the tablets of Examples 13 and 14-1 and Comparative Examples 2 and 3.

The solubilities of the tablets of Examples 13 and 14-1, and Comparative Examples 2 and 3 were investigated using the same conditions discussed in Test Example 1. Three tablets of each formulation containing paclitaxel of Examples 13 and 14-1, and Comparative Examples 2 and 3 (equivalent to 90 mg of paclitaxel) were introduced into dissolution tester (Labfine, Korea). The solubility profiles of all the formulations are shown in FIG. 5.

Among the samples tested, the tablet of Example 14-1, prepared by the fluid bed spray dry technology, showed the fastest and highest solubility. The dissolution rate was very fast and highest dissolution/solubility occurred within 20 min. This could be due to faster disintegration of tablet attributed to the process of preparation and faster dissolution of amorphous paclitaxel by the solid dispersion containing hydrophilic polymer and surfactants.

The tablet of Example 13, prepared by the traditional spray drying technology, showed comparatively slower and lower dissolution and solubility profile compared to that of Example 14-1, and complete dissolution occurred around 40 min. The tablet of Comparative Example 2, prepared by fluid bed spray drying technology and with highest amount of polymer content, showed the slowest disintegration and dissolution compared to other formulations tested. Despite being amorphous, the slow release and low solubility could be attributable to the highest polymer content that prevents fast hydration and release. The tablet of Comparative Example 3, prepared by conventional tabletting method, showed slow release and low solubility than the tablets of Examples 13 and 14-1, and the solubility was comparable to Comparative Example 2. From this test results, it is understandable that neither crystalline paclitaxel of Comparative Example 3 nor high polymer content of Comparative Example 2 produced expected solubility.

Test Example 6: Disintegration Test of Tablets of Examples 13 and 14-1 and Comparative Examples 2 and 3

The tablet of Example 13 prepared by the traditional spray drying technology, the tablet of Example 14-1 prepared by the fluid bed spray drying technology, the tablet of Comparative Example 2 with the highest polymer ratio and only SLS, and the conventional tablet of Comparative Example 3 were subjected to disintegration test as per United States Pharmacopoeia (USP). The disintegration time of the respective tablets are shown in Table 13.

The tablet of Example 14-1 showed shorter disintegration time compared to that of Example 13. The disintegration time for Comparative Example 2 with highest polymer ratio and only SLS was highest. The faster disintegration of Example 14-1 could be attributable to the fluid bed process technology which imparts lower density granules with highly porous surface which are easily wettable and so faster disintegration.

TABLE 13

| Formulation | Disintegration time (min) |
| --- | --- |
| Comparative Example 2 | >40 ± 5 |
| Comparative Example 3 | 20 ± 5 |
| Example 13 | 9 ± 2 |
| Example 14-1 | 5 ± 1 |

Test Example 7: Solid State Characterization of Tablets of Example 13 and 14-1, and Paclitaxel API The solid-state characterization of the spray dried tablet of Example 13 prepared by the traditional spray drying process, the spray dried tablet of Example 14-1 prepared by the fluid bed spray drying process, and paclitaxel API was evaluated by XRD using M18XHF-SRA (Macsciences Co., Ltd., Japan) under the conditions of Cu X-ray, 40 kV and 100 mA, with a scan speed of 6°/min.

Figure 6A:
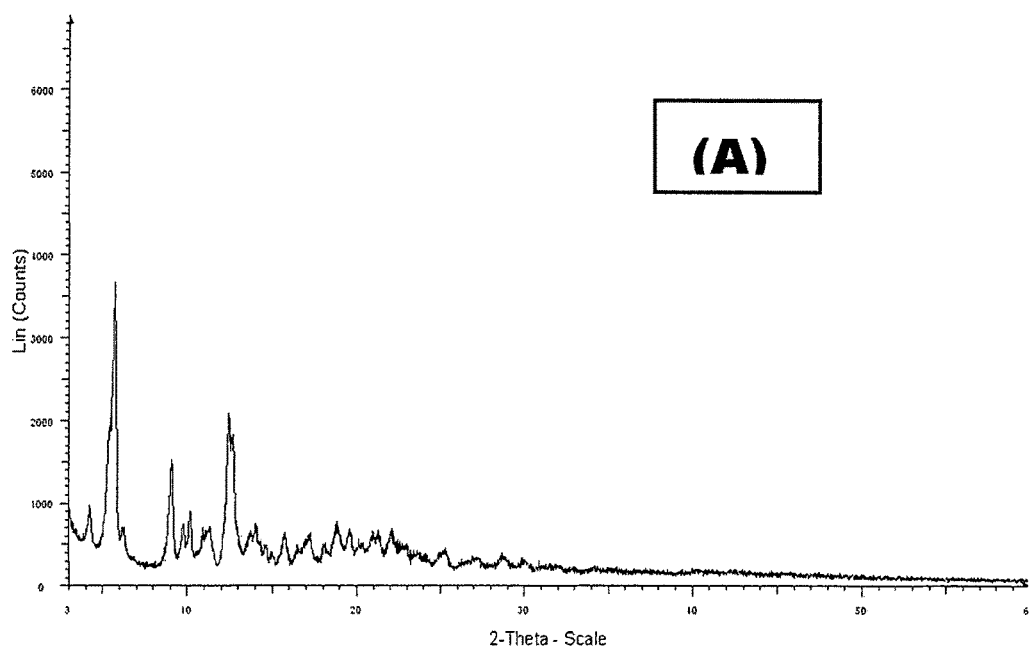
FIG. 6 shows the X-ray diffraction pattern of (A) paclitaxel API; (B) the tablet of Example 13; and (C) the tablet of Example 14-1.
Figure 6B:
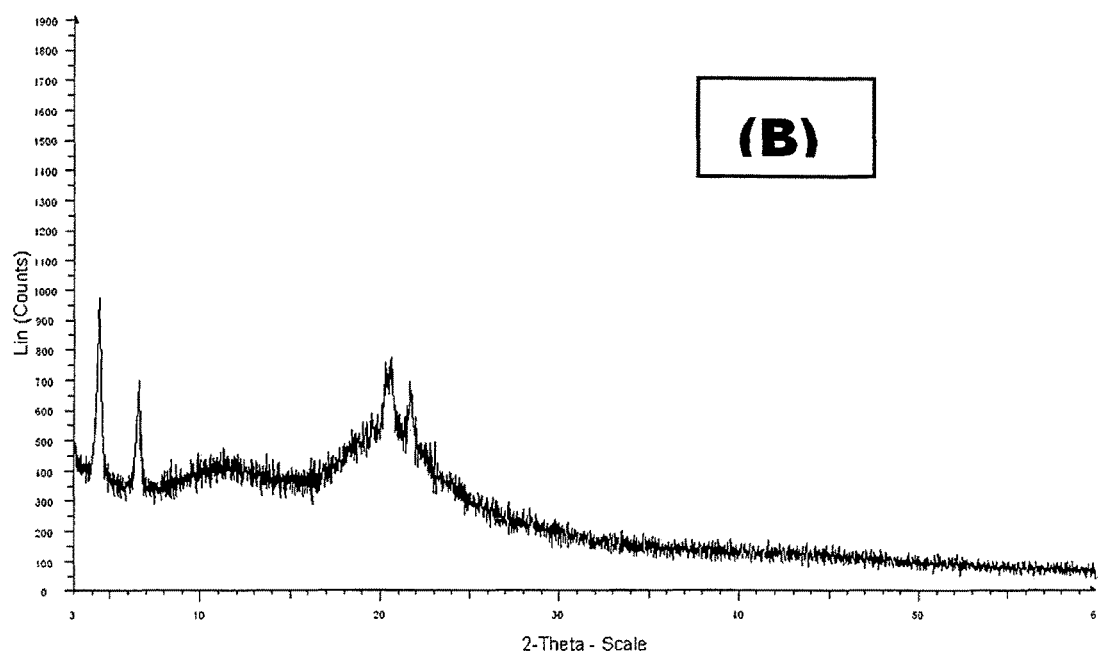
Figure 6C:
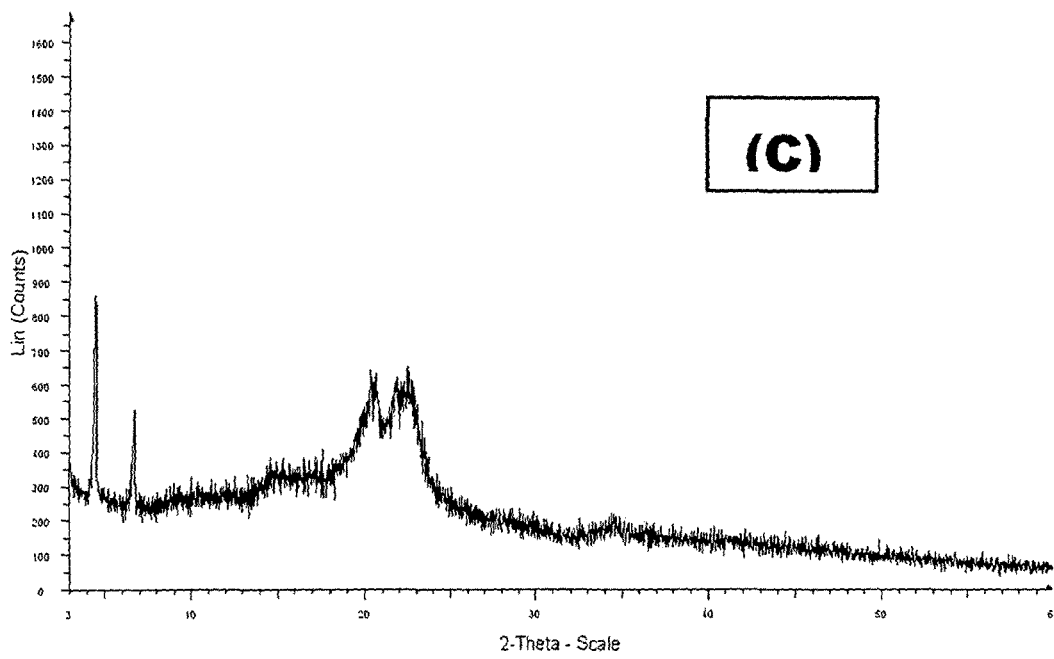

The results of X-ray diffraction patterns of paclitaxel API, and the tablets of Examples 13 and 14-1 were shown in FIG. 6. As shown in FIG. 6A, the active ingredient, paclitaxel, had peaks at two-theta (degree) 4.147, 5.224, 5.600, 6.138, 8.987, 9.711, 10.123, 11.195, 12.454, 13.690, 13.967, 15.682, 16.481, 17.144, 18.051, 18.791, 19.541, 20.191, 21.248, 22.022, 22.822, 23.558, 25.227, 26.339, 27.119, 28.689, 29.985, 31.963, 32.855, and 34.178. However, as shown in FIGS. 6B and 6C, the tablets of Examples 13 and 14-1 did not show any peaks because the spray drying process converted the crystalline active ingredient into amorphous form, resulting in amorphous solid dispersion composition.

Test Example 8: Comparison of In Vivo PK Parameters and Bioavailability of Tablets of Examples 13 and 14-1, and Comparative Example 3 in Beagle Dogs In vivo dog bioavailability and pharmacokinetic studies were performed to investigate the increase in bioavailability of the tablets of Examples 13 and 14-1, and Comparative Example 3.

Dogs (beagle dogs weighing around 10~15 kg) were fasted overnight prior to dosing, but are permitted water ad libitum. The dogs were separated into three groups for Examples 13 and 14-1, and Comparative Example 3, and each dog received 30 mg of Pgp inhibitor orally approximately 30 minutes prior to dosing of paclitaxel formulations.

After 30 minutes, each dog was administered with the tablets equivalent to 60 mg of paclitaxel. The dose was followed by approximately 150 mL of water. Blood samples were obtained from each animal prior to dosing and at 0.25, 0.5, 1.0, 1.5, 2, 3, 4, 6, 8, 10, 12, and 24 hours after drug administration. The plasma is separated by centrifugation and frozen (−40° C.) until analysis. The concentration of paclitaxel in the plasma was determined by reverse phase HPLC with low wavelength UV detection following liquid-liquid extraction of the plasma samples. Paclitaxel area under the curve is calculated by the trapezoidal method over the time course of the study. The values reported are averages for each group of dogs in Table 14.

TABLE 14

| PK Parameters | Example 13 | Example 14-1 | Comp. Ex. 3 |
| --- | --- | --- | --- |
| $AUC_{last}$ (ng · hr/mL) | 781.15 ± 418.93 | 898.36 ± 318.51 | 223.38 ± 160.91 |
| $AUC_{inf}$ (ng · hr/mL) | 802.85 ± 404.99 | 990.01 ± 321.27 | 234.85 ± 185.42 |
| $C_{max}$ (ng/mL) | 136.35 ± 111.74 | 172.89 ± 71.26 | 38.85 ± 39.34 |
| $T_{max}$ (hr) | 1.45 ± 0.64 | 0.98 ± 0.37 | 2.08 ± 1.5 |
| $t_{1/2}$ (hr) | 15.03 ± 3.73 | 13.83 ± 2.34 | 10.45 ± 4.64 |

Figure 7:
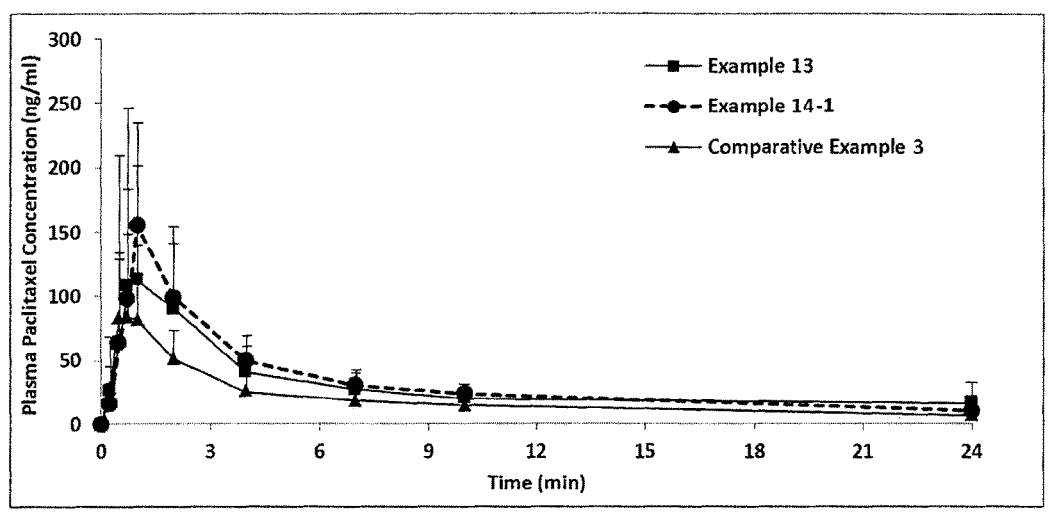
FIG. 7 shows the pharmacokinetic profiles of the tablets of Examples 13 and 14-1, and Comparative Example 3 in beagle dogs.

FIG. 7 shows the pharmacokinetic profiles of the tablets of Examples 13 and 14-1, and Comparative Example 3 in beagle dogs. All data were listed as mean of six with standard deviation. The profiles were plotted with plasma concentration (ng/mL) against time. The FIG. 7 and Table 14 show that the tablet of Example 14-1 demonstrated highest bioavailability with highest $C_{max}$. While, the Comparative Example 3 prepared by conventional method showed lowest bioavailability.

The $T_{max}$ was shorter and $t_{1/2}$ was higher for the tablets of Examples 13 and 14-1. AUC of the tested tablets were higher for the tablets of Examples 13 and 14-1 as compared to Comparative Example 3 prepared by conventional method. Besides, the inter-individual variations for the solid dispersions of Examples 13 and 14-1 were comparatively lower compared to the Comparative Example 3.

The enhanced $C_{max}$ and AUC coupled with reduced $T_{max}$ could be due to the matrix of water soluble polymer and amorphous drug that enhances the solubility in vivo and preventing precipitation leading to enhanced absorption of paclitaxel.

It is clearly demonstrated that the administration of the tablet containing paclitaxel solid dispersion in dogs resulted in enhanced solubility and bioavailability.

Test Example 9: Stability of Tablet of Example 14-1 at Accelerated Condition The tablet of Example 14-1 was stored under accelerated conditions according to the following protocol. The amount of degradation products of each active ingredient was measured to compare the stability of the composite formulations. The results are shown in Table 16.

Accelerated Storage Conditions

Storage conditions: contained in an HDPE bottle @ 40° C., 75% RH

Test duration: initial, 1 and 3 months

Analysis target: paclitaxel and related compounds

Analysis Conditions of Paclitaxel and its Related Compounds

Column: Stainless column (internal diameter of about 4.6 mm and length of 15 cm) packed with octadecylsilyl silica gel for liquid chromatography (e.g., Symmetry C18, 3 μm particle size)

Mobile phase: A: Acetonitrile: Water (7:3); B: Acetonitrile

Detector: UV-absorption detector (absorbance at 227 nm)

Flow rate: 1.2 mL/min

Injection volume: 10 μL

Column temperature: 35° C.

Gradient system:

TABLE 15

| Time (min) | Eluent A (%) | Eluent B (%) |
|---|---|---|
| 0~26 | 100 | 0 |
| 26~66 | 100→17 | 0→83 |
| 66~67 | 17→100 | 83→0 |
| 67~75 | 100 | 0 |

TABLE 16

| Impurities | RRT | Limit (NMT) | Initial | Month-1 | Month-3 |
|---|---|---|---|---|---|
| Baccatin III | 0.19 | 0.80 | 0.022 | 0.028 | 0.032 |
| Ethyl ester side chain | 0.21 | 0.40 | 0.000 | 0.000 | 0.00 |
| 10-Deacetylpaclitaxel | 0.50 | 0.80 | 0.000 | 0.073 | 0.085 |
| 2-Benzoylpaclitaxel-2-pentenoate | 0.80 | 0.70 | 0.000 | 0.000 | 0.00 |
| 10-Deactyl-7-epipaclitaxel | 0.95 | 0.50 | 0.018 | 0.028 | 0.035 |
| 7-epipaclitaxel | 1.40 | 0.60 | 0.075 | 0.072 | 0.081 |
| UK-1 (RRT-0.18) | 0.18 | 0.20 | 0.000 | 0.030 | 0.033 |
| UK-2 | 1.05 | 0.20 | 0.029 | 0.000 | 0.000 |
| UK-2 | 1.10 | 0.20 | 0.000 | 0.000 | 0.000 |
| Total Impurities | | | 0.231 | 0.438 | 0.476 |

According to the results, the stability of the tablet solid dosage formulation of Example 14-1 was excellent for up to 3 months in the accelerated condition. All known and unknown impurities were within the specified limits mentioned in USP.

Accordingly, this inventive method of preparing a tablet containing the paclitaxel solid dispersion prepared by traditional spray drying method or fluid bed spray drying method and pharmaceutical excipients would have advantage over other methods and could be utilized for oral administration of paclitaxel, especially as an oral solid dosage formulation. This inventive method of preparing a tablet containing paclitaxel solid dispersion proved to be highly stable, soluble, and highly bioavailable in vivo.

Although the present invention has been described by way of a detailed description in which various embodiments and aspects of the invention have been described, it will be seen by one skilled in the art that the full scope of this invention is not limited to the examples presented herein. Therefore, the substantial scope of the present invention will be defined by the accompanying claims and equivalents thereof.

What is claimed is:

1. An amorphous solid dispersion comprising a taxane or a pharmaceutically acceptable salt thereof, polyvinylpyrrolidone, polysorbate, and sodium lauryl sulfate.

2. The amorphous solid dispersion of claim 1, wherein the taxane is any one selected from the group consisting of paclitaxel, docetaxel, cabazitaxel, larotaxel, ortataxel, tesetaxel, and a combination thereof.

3. The amorphous solid dispersion of claim 1, wherein the taxane is paclitaxel.

4. The amorphous solid dispersion of claim 1, wherein the polyvinylpyrrolidone is polyvinylpyrrolidone K-30.

5. The amorphous solid dispersion of claim 1, wherein the weight ratio of the polyvinylpyrrolidone and the taxane is in the range of 2:1 to 9:1.

6. The amorphous solid dispersion of claim 5, wherein the weight ratio of the polyvinylpyrrolidone and the taxane is 2.5:1 to 3.5:1.

7. The amorphous solid dispersion of claim 1, wherein the polysorbate is polysorbate 80.

8. The amorphous solid dispersion of claim 1, wherein the weight ratio of polysorbate to sodium lauryl sulfate is 1:5 to 5:1.

9. The amorphous solid dispersion of claim 1, wherein the weight ratio of the taxane to the combined weight of polysorbate and sodium lauryl sulfate is 1:1 to 1:3.

10. The amorphous solid dispersion of claim 1, wherein the weight ratio of the combined weight of polysorbate and sodium lauryl sulfate to the polyvinylpyrrolidone is 1:1 to 1:5.

11. The amorphous solid dispersion of claim 1, wherein polyvinylpyrrolidone is in an amount of 10% to 80% by weight based on the total amount of the solid dispersion.

12. The amorphous solid dispersion of claim 11, wherein polyvinylpyrrolidone is in an amount of 40% to 60% by weight based on the total amount of the solid dispersion.

13. The amorphous solid dispersion of claim 1, wherein the combined weight of polysorbate and sodium lauryl sulfate is 10% to 50% by weight based on the total amount of the solid dispersion.

14. The amorphous solid dispersion of claim 13, wherein the combined weight of polysorbate and sodium lauryl sulfate is 30 to 40% by weight based on the total amount of the solid dispersion.

15. The amorphous solid dispersion of claim 1, wherein the weight ratio of the polyvinylpyrrolidone to the taxane is about 3:1 and the weight ratio of the taxane to the combined weight of polysorbate and sodium lauryl sulfate is about 1:2.

16. The amorphous solid dispersion of claim 1, which is prepared by spray drying.

17. A tablet comprising the amorphous solid dispersion of claim 1, an intragranular excipient, and an extragranular excipient.

18. The tablet of claim 17, wherein the amorphous solid dispersion is in an amount of 15% to 50% by weight, based on the total weight of the tablet.

19. The tablet of claim 18, wherein the amorphous solid dispersion is in an amount of 20 to 30% by weight, based on total tablet weight.

20. The tablet of claim 17, wherein the intragranular and extragranular excipients are each selected from the group consisting of fillers, disintegrants, lubricants, surfactants, and a mixture thereof.

21. The tablet of claim 17, wherein the intragranular excipient is selected from the group consisting of microcrystalline cellulose, croscarmellose sodium, sodium lauryl sulfate, and a mixture thereof.

22. The tablet of claim 17, wherein the extragranular excipient is selected from the group consisting of microcrystalline cellulose, croscarmellose sodium, sodium stearyl fumarate, and a mixture thereof.

23. A method for preparing the amorphous solid dispersion of claim 1, comprising the steps:
   (a) dissolving a taxane or a pharmaceutically acceptable salt thereof, polyvinylpyrrolidone, polysorbate, and sodium lauryl sulfate in a solvent; and
   (b) drying the solution obtained in step (a).

24. The method of claim 23, wherein step (b) comprises spray drying.

25. The method of claim 23, wherein the taxane is dissolved in an organic solvent.

26. The method of claim 23, wherein the polyvinylpyrrolidone, polysorbate, and sodium lauryl sulfate is dissolved in an aqueous organic solvent.

27. The method of claim 26, wherein the aqueous organic solvent comprises a mixture of ethanol and water.

28. A method for preparing the tablet of claim 17, comprising the steps:
   (a) dissolving a taxane or a pharmaceutically acceptable salt thereof, polyvinylpyrrolidone, polysorbate, and sodium lauryl sulfate in a solvent;
   (b) drying the solution obtained in step (a) to produce a solid dispersion;
   (c) mixing together the solid dispersion with an extragranular excipient; and
   (d) compressing the resulting mixture to form a tablet.

29. The method of claim 28, wherein step (b) comprises spray drying.

30. The method of claim 29, wherein the spray drying is conducted in a fluid bed.

31. The method of claim 30, wherein the fluid bed comprises an intragranular excipient.

32. The method of claim 28, wherein the polyvinylpyrrolidone, polysorbate, and sodium lauryl sulfate is dissolved in an aqueous organic solvent.

33. The method of claim 32, wherein the solvent aqueous organic solvent comprises a mixture of ethanol and water.

* * * * *